United States Patent [19]

Arnold et al.

[11] Patent Number: 4,791,110
[45] Date of Patent: Dec. 13, 1988

[54] FUNGICIDAL PYRIDAZINES

[75] Inventors: Wendell R. Arnold, Carmel, Ind.; William C. Dow, Hayward, Calif.; George W. Johnson, Greenfield, Ind.

[73] Assignee: Eli Lilly and Company, Indianapolis, Ind.

[21] Appl. No.: 859,558

[22] Filed: May 5, 1986

Related U.S. Application Data

[63] Continuation-in-part of Ser. No. 744,722, Jun. 14, 1985, abandoned.

[51] Int. Cl.$^4$ .................. A01N 55/00; A01N 43/58; C07D 237/12; C07D 405/12
[52] U.S. Cl. .................................. 514/247; 544/224; 544/229; 544/238
[58] Field of Search ............... 544/224, 241, 229; 71/92

[56] References Cited

U.S. PATENT DOCUMENTS

| | | | |
|---|---|---|---|
| 3,023,208 | 2/1962 | Chambers et al. | 260/250 |
| 3,883,530 | 5/1975 | Bublitz | 260/250 |
| 4,143,144 | 3/1979 | Tobol et al. | 424/263 |
| 4,263,297 | 4/1981 | Rothgery et al. | 424/250 |
| 4,412,079 | 10/1983 | Cebalo et al. | 548/141 |

FOREIGN PATENT DOCUMENTS 2531476  7/1975  Fed. Rep. of Germany .

OTHER PUBLICATIONS

Chambers, Chem. Abs. 83, 114324c (1975).
Dow Technical Information Leaflet (undated), Dowco 444 Systemic Fungicide.
Herbicide Handbook of the Weed Science Society of America, 4th Ed., 1979, pp. 193-194.

Primary Examiner—Mark L. Berch
Attorney, Agent, or Firm—Donald R. Stuart; Leroy Whitaker; Joseph A. Jones

[57] ABSTRACT

Plants are protected from the damaging effects of Phycomycetous fungi by a series of pyridazines of formula

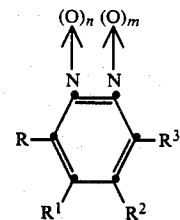

wherein
$R^3$ is chloro, bromo, methyl, cyano or iodo;
R is chloro, bromo, iodo, methyl, cyano or furan-2-ylmethoxy;
$R^1$ is hydrogen, methyl, ethyl or n-propyl;
$R^2$ is

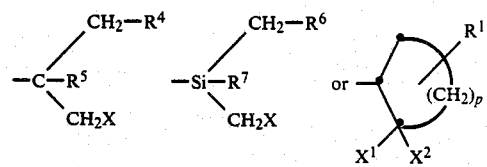

X is fluoro, chloro, bromo or iodo;
$X^1$ and $X^2$ independently represent X or hydrogen, provided that no more than one of $X^1$ and $X^2$ is hydrogen;
$R^4$ is hydrogen, chloro, bromo, methyl or ethyl;
$R^5$ is hydrogen, chloro, methyl, ethyl, chloromethyl or dichloromethyl;
or $R^4$ and $R^5$ combine with the group to which they are attached to form a $C_3$-$C_7$ cycloalkyl group substituted with a $R^1$ group;
$R^6$ is hydrogen, chloro, bromo, methyl or ethyl;
$R^7$ is hydrogen, methyl, ethyl, chloromethyl or dichloromethyl;
one of m and n is 0 or 1, and the other is 0;
p is 0–4.

45 Claims, No Drawings

FUNGICIDAL PYRIDAZINES

CROSS-REFERENCE

This application is a continuation-in-part of copending application Ser. No. 744,722, filed June 14, 1985 abandoned.

BACKGROUND OF THE INVENTION

1. Field of the Invention

The present invention belongs to the fields of agricultural and organic chemistry, and provides to the art a series of new 4-(halo-branched-alkyl or silyl)pyridazines, which are fungicides for the protection of plants from harmful pathogens. The compounds are effective against Phycomycetous fungi, which include some of the most injurious plant pathogens. In particular, the compounds are effective against *Phytophthora infestans*, which is the causative organism of late blight of potato and tomato and which caused the terrible potato famine of 1845.

2. State of the Art

Halo-branched-alkyl heterocycles have not previously been studied in the plant protection art. Earlier work has focused on compounds such as those of U.S. Pat. No. 3,883,530, which teaches di- and trichloromethylpyridazines having from 2 to 3 chlorine atoms on the heterocyclic ring. U.S. Pat. No. 4,263,297 shows a 3-trichloromethylpyridazine having an alkoxy group at the 6-position. Both patents describe their compounds as fungicides and bactericides.

West German Patent application No. 2,531,476 shows 3,6-dichloro-4-trichloromethylpyridazine, also described as a fungicide.

Dow Chemical formerly sold a fungicide, active against Phycomycetes, called pyroxyfur, which is 2-chloro-6-(furan-2-ylmethoxy)-4-trichloromethylpyridine.

SUMMARY OF THE INVENTION

The present invention provides a series of pyridazines of the formula

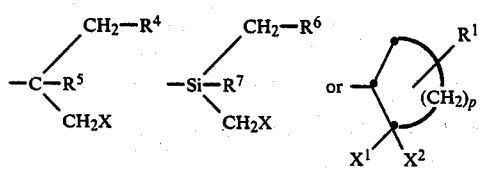

wherein
$R^3$ is chloro, bromo, methyl, cyano or iodo;
R is chloro, bromo, iodo, methyl, cyano or furan-2-ylmethoxy;
$R^1$ is hydrogen, methyl, ethyl or n-propyl;
$R^2$ is

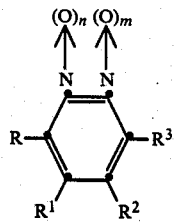

X is fluoro, chloro, bromo or iodo;
$X^1$ and $X^2$ independently represent X or hydrogen, provided that no more than one of $X^1$ and $X^2$ is hydrogen;
$R^4$ is hydrogen, chloro, bromo, methyl or ethyl;
$R^5$ is hydrogen, chloro, methyl, ethyl, chloromethyl or dichloromethyl;
or $R^4$ and $R^5$ combine with the group to which they are attached to form a $C_3$-$C_7$ cycloalkyl group substituted with a $R^1$ group;
$R^6$ is hydrogen, chloro, bromo, methyl or ethyl;
$R^7$ is hydrogen, methyl, ethyl, chloromethyl or dichloromethyl;
one of m and n is 0 or 1, and the other is 0;
p is 0–4.

The invention also provides a method of reducing the adverse effects of Phycomycetous fungi on plants which comprises applying a Phycomycete-inhibiting amount of a compound of the invention to the plant or to the soil in which it grows.

The invention also provides fungicidal compositions which comprise a compound of the invention and a phytologically-acceptable carrier.

The invention further provides fungicidal combination compositions and methods comprising a compound of the invention in combination with a dithiocarbamate fungicide of the formula

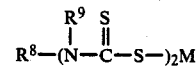

wherein
$R^8$ is $C_1$-$C_4$ alkylene;
$R^9$ is $C_1$-$C_3$ alkyl or hydrogen;
M is a divalent metal ion or two monovalent metal ions;

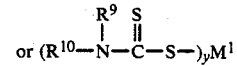

wherein
y is 1–3;
$M^1$ is a metal ion of valence 1–3;
$R^{10}$ is $C_1$-$C_4$ alkyl.

DESCRIPTION OF THE PREFERRED EMBODIMENTS

The Compounds

Throughout this document, all temperatures will be described in degrees Celsius. All expressions of percentage, proportion and the like will be in weight units unless otherwise stated.

In the structural formula above, all of the chemical terms carry their conventional meanings.

While the above structural formula is believed to describe the compounds unambiguously, a group of the exemplary compounds will be mentioned to assure that the reader fully understands the invention.

3,6-dichloro-4-(1-bromomethylethyl)pyridazine
3,6-dichloro-4-(1-chloromethyl-1-methylethyl)-5-propylpyridazine
3,6-dichloro-4-(1-fluoromethylpropyl)-5-propylpyridazine
4-(1-bromomethyl-1-chloromethylpropyl)-3-chloro-6-(furan-2-ylmethoxy)pyridazine 3,6-dichloro-4-(1-chloromethyl-1-iodomethylbutyl)-5-methylpyridazine
3-chloro-4-(1-dichloromethyl-1-fluoromethylethyl)-6-(furan-2-ylmethoxy)pyridazine
3-chloro-4-(1-chloromethylethyl)-6-(furan-2-ylmethoxy)pyridazine
4-(1-bromomethyl-1-ethylbutyl)-3,6-dichloro-5-ethylpyridazine
3,6-dichloro-4-(1-chloromethyl-1-iodomethylpropyl)pyridazine
3,6-dichloro-4-(1-bromomethyl-1-chloromethylethyl)-5-methylpyridazine, N²-oxide
4-(1-bromomethyl-1-methylpropyl)-3-chloro-6-(furan-2-ylmethoxy)pyridazine, N¹-oxide
3-bromo-4-(1-bromomethyl-1-chloro-2-chloroethyl)-6-methylpyridazine
4-(2-bromo-1-chloro-1-methylethyl)-3-chloro-6-cyanopyridazine, N²-oxide
4-(1-bromomethyl-1-fluoromethylpropyl)-5-ethyl-3,6-diiodopyridazine
4-(1-chloro-1-iodomethylbutyl)-3,6-dimethylpyridazine
3,6-dibromo-4-(1-chloromethylcyclopropyl)-5-methylpyridazine
4-(1-bromomethyl-2-methylcyclobutyl)-3,6-dicyanopyridazine
3-bromo-6-cyano-4-(4-ethyl-1-fluoromethylcyclohexyl)pyridazine
6-cyano-3-iodo-4-(1-iodomethyl-3-propylcycloheptyl)-5-propylpyridazine
4-(chloromethyl)(dichloromethyl)methylsilyl-6-(furan-2-ylmethoxy)-3-methylpyridazine
4-(chloromethyl)(iodomethyl)ethylsilyl-3-cyano-5-ethyl-6-(furan-2-ylmethoxy)pyridazine, N¹-oxide
4-(bromomethyl)(chloromethyl)fluoromethylsilyl-6-(furan-2-ylmethoxy)-3-iodopyridazine
3-bromo-4-(bromomethyl)(chloromethyl)ethylsilyl-6-(furan-2-ylmethoxy)pyridazine
4-(bromomethyl)(methyl)ethylsilyl-3,6-dichloropyridazine
3-bromo-4-(chloromethyl)(iodomethyl)silyl-6-cyanopyridazine
6-bromo-4-(chloromethyl)(dichloromethyl)methylsilyl-3-methylpyridazine, N²-oxide
4-(fluoromethyl)methylsilyl-6-iodo-3-methylpyridazine
6-bromo-4-(bromomethyl)(chloromethyl)ethylsilyl-3-chloropyridazine
6-bromo-4-(bromomethyl)(methyl)ethylsilyl-3-chloropyridazine
3,6-dichloro-4-(2-fluorocyclopropyl)pyridazine
4-(2-bromocyclopentyl)-3,6-diiodopyridazine, N¹-oxide
4-(2-iodo-3-methylcyclobutyl)-3,6-dimethylpyridazine
4-(2-chlorocycloheptyl)-6-(furan-2-ylmethoxy)-3-methylpyridazine
3-bromo-4-(2-ethyl-6-iodocyclohexyl)-6-methylpyridazine
6-bromo-4-(2-chloro-4-propylcyclopentyl)-3-methylpyridazine
6-bromo-4-(2-fluorocyclopropyl)-3-iodopyridazine
3-bromo-4-(2-bromo-5-methylcyclohexyl)-6-iodopyridazine
3,6-dichloro-4-(2-chlorocycloheptyl)pyridazine
3-bromo-4-(2-chlorocyclobutyl)-6-cyanopyridazine While all of the compounds of the present invention are useful and desirable for fungicidal purposes, certain classes of the compounds are preferred.

The following formula shows one preferred class of compounds.

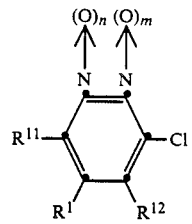

wherein
R¹¹ is chloro or furan-2-ylmethoxy;
R¹² is

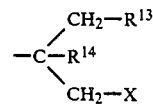

R¹³ is hydrogen, chloro, methyl or ethyl;
R¹⁴ is hydrogen, methyl, ethyl, chloromethyl or dichloromethyl;
R¹, X, m and n are defined above.

The following group of limitations describe other preferred classes of the compounds. It will be understood that the limitations described below can be combined to create further groups of preferred compounds.

(a) R is chloro, bromo or methyl;
(b) R is chloro or bromo;
(c) R is chloro;
(d) R³ is chloro, bromo or methyl;
(e) R³ is chloro or bromo;
(f) R³ is chloro;
(g) R³ is furan-2-ylmethoxy;
(h) R¹ is hydrogen;
(i) R² is

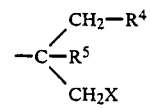

(j) R² is

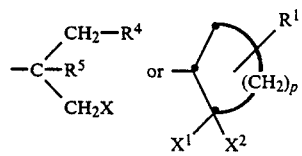

(k) X is bromo or chloro;
(l) X is fluoro or iodo;
(m) R⁴ is hydrogen, chloro or bromo;
(n) R⁴ is hydrogen or chloro;
(o) R⁴ is methyl or ethyl;
(p) R⁴ is hydrogen;
(q) R⁵ is hydrogen, chloro or methyl;
(r) R⁵ is hydrogen, methyl or ethyl;
(s) R⁵ is chloromethyl or dichloromethyl;
(t) R⁵ is methyl;
(u) R⁵ is hydrogen or ethyl;
(v) m and n are 0.

Synthesis

The compounds of the present invention present some interesting synthetic steps, but are made by processes which, in general, parallel those in the art for the synthesis of related compounds.

The key intermediate for the preparation of the compounds is the pyridazine which has the R and $R^3$ groups in place. The 3,6-dichloropyridazine is a commercial product. Other halogenated intermediates are prepared in manners analogous to the preparation of the dichloro compound. For example, the dibromopyridazine is most conveniently prepared by reacting 3,6-dioxopyridazine with phosphorus oxybromide. The other halogenated pyridazines are prepared analogously.

Intermediates having one halogen at the 3-position and another at the 6-position are prepared by displacing a bromine or chlorine atom with a halogenating reagent, conveniently, with a lithium halide.

Intermediates having one methyl group are prepared, for example, by reacting levulinic acid with hydrazine to prepare 3-methyl-6-oxopyridazine, which compound can be halogenated, as with phosphorus oxychloride, to prepare a 3-methyl-6-halo intermediate. Intermediates having a methyl at both the 3- and 6-positions are most conveniently prepared from 2,5-dimethylfuran, which is reacted with methanol in the presence of bromine to give the 2,5-dimethyl-2,5-dimethoxy compound. That intermediate is reacted with hydrazine to give the desired 3,6-dimethyl intermediate.

Intermediate pyridazines having a cyano group are conveniently prepared from the corresponding carboxylic acids, by converting the acid to an amide, and dehydrating the amide to form the desired cyano group.

The group $R^2$ is put in place on the 3,6-di-substituted pyridazine by processes which are referred to, in general, as alkylation. The alkylation processes will be discussed with reference to the preferred group

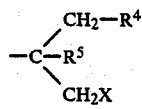

Alkylations to put other $R^2$ groups in place will then be more briefly discussed.

The preferred first step is an alkylation with a propanediol of the formula

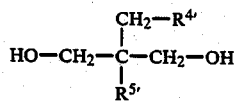

wherein $R^{4'}$ and $R^{5'}$ represent the non-halogenated definitions of the groups $R^4$ and $R^5$. For example, if the group $R^5$ is to be chloromethyl in the product, the group $R^{5'}$ will be methyl in formula A.

The starting compound of formula A is used to alkylate the pyridazine in an alkylation of the type which has been described in many articles by Minisci and coworkers. In general, the reaction goes in the presence of silver ion and persulfate ion ($S_2O_8^{--}$) in an aqueous acid, preferably sulfuric acid or trifluoroacetic acid. The process is carried out at moderate temperatures, in the range of from about the ambient temperature to about 100°, and the alkylations produce economically useful yields in moderate periods of time in the range of from several minutes to several hours. It is advisable to use a substantial excess of the propanediol alkylating agent, and a substantial excess of the persulfate as well. An amount of silver ion in the range of from about a few tenths of a mole, to about one mole per mole of product to be obtained is effective. It is preferred to use a relatively large amount of silver ion and recover the silver.

The alkylation conditions remove one of the hydroxymethyl groups from the propanediol, in the form of formaldehyde, and produce a product wherein the 4-position of the pyridazine is occupied by a group of the formula

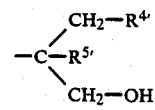 B

Alternatively, the alkylation is performed with a hydroxypropanaldehyde of the formula

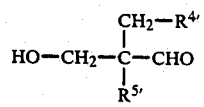 A1

Use of the aldehyde has the advantage that the alkylation can be done without the presence of silver ion. In other respects, alkylations with the aldehyde are carried out under the same conditions as alkylations with the propanediol, and the same group of formula B is provided at the 4-position of the pyridazine.

The hydroxy group of the group of formula B is replaced by a halogen to provide the group X of the compounds of this invention. Conventional halogenating agents are used. When X is to be chloro, the preferred agent is thionyl chloride, used in the presence of pyridine under anhydrous conditions. Temperatures in the range of about 50°–100° give economically-acceptable yields of the chlorinated product in several hours. Example 1 below illustrates the process.

Another convenient way to provide the halogen atom X is first to esterify the compound having the group of formula B with an acid, of which p-toluenesulfonic acid is particularly convenient. Reaction of the compound with, for example, p-toluenesulfonyl chloride, usually in the presence of an acid scavenger, provides the desired ester. That compound can be halogenated with simple halides, such as lithium bromide, potassium iodide, lithium chloride and the like, to provide the desired compound wherein X is the corresponding halogen atom.

As is well known, suitable fluorinating agents are few, because of the great stability of fluorine compounds. One compound which can be used to replace the hydroxy group of the group of formula B with fluorine is diethylaminosulfur trifluoride. The reaction is carried out under basic conditions, in the presence of a strong organic base such as triethylamine, pyridine and the like, in a highly stable solvent, such as halogenated alkane. Dichloromethane, chloroform and the like are suitable. The reaction should be carried out under anhydrous conditions and at low temperatures, in the range of about −25° to 25°.

When the groups $R^4$ and $R^5$ include halogen atoms, the compound is halogenated by conventional means. It is preferred, in most cases, to carry out such halogenations after the halogen atom X has been inserted, unless all halogens in the group are the same.

The halogenations of the groups R⁴′ and R⁵′ are carried out under free radical conditions, usually in the presence of activating energy such as strong light, and preferably in the presence of a radical initiator. Convenient halogenating agents for use under such conditions include, for example, sulfuryl chloride, N-iodosuccinimide, N-bromosuccinimide, N-chlorosuccinimide, and the like. Organic peroxides are the preferred initiators, of which benzoyl peroxide is particularly useful. Other initiators, for example, azo-bis-isobutyronitrile, t-butyl hydroperoxide and the like, can also be used if desired. Only a catalytic amount of the initiator is needed. The processes are carried out in highly inert solvents, of which halogenated alkanes such as carbon tetrachloride are preferred. Such reactions are carried out at moderate temperatures, in the range of from about the ambient temperature to about 100°, and are often most effectively carried out continuously in equipment which flows the reaction mixture in a thin film past the strong light which provides activating energy.

If it is desired to avoid the use of a propanediol or propanaldehyde intermediate, the pyridazine intermediate can be alkylated with the alkanoic acid which corresponds to the $R^2$ group without the halogen atoms in place. For example, if $R^2$ is to be 1-chloromethyl-1-methylethyl, the alkanoic acid would be pivalic acid. The alkylation is carried out under Minisci conditions, substantially as discussed above for alkylations with a propanediol. When such a starting compound is used, the group X must be placed by a halogenation under free radical conditions, as described above, as are other chlorine atoms in the groups $R^3$ and $R^4$.

When the $R^2$ group is an alkylsilyl group, it is put in place by a free radical technique. The halogen atoms of the silyl $R^2$ group can be in place on the starting compound. The process is conveniently carried out in the presence of a radical initiator, such as was described above, under high-energy conditions such as strong light. It is very important to carry out the silylation under perfectly dry conditions. The silyl intermediate may have a hydrogen atom as the fourth bond to the silicon atom, or may have a halogen.

When the $R^2$ group is one wherein $R^4$ and $R^5$ combine to form a cycloalkyl group, it is most conveniently prepared by starting with a 1,1-di(hydroxymethyl)cycloalkyl intermediate. The alkylation is carried out under Minisci conditions as described above to prepare a 1-hydroxymethylcycloalkyl group. The hydroxymethyl group is then halogenated as has been discussed in detail.

The preparation of halocycloalkyl groups conveniently begins with a cycloalkene intermediate. The alkylation is carried out under Minisci conditions to prepare the compound having a 2-hydroxycycloalkyl substituent at the 4-position. The hydroxy group is replaced with a halogen atom in the same way that other halogenations are carried out.

When the desired product has a 5-alkyl substituent, that substituent is preferably inserted as a later step, by an alkylation with the corresponding alkanoic acid under Minisci conditions as described above. For example, if a 5-methyl group is desired, the compound is alkylated with acetic acid; if a propyl group is desired, it is alkylated with butyric acid.

When a product is desired wherein R is furan-2-ylmethoxy, the 6-chlorine atom is replaced by a simple reaction with furan-2-ylmethanol, carried out in the presence of an acid scavenger such as a strong inorganic or organic base. Strong bases such as alkali metal hydrides and hydroxides, alkyllithium compounds, and dialkylamides, especially butyllithium and diisopropyl amide, are particularly useful. The process is carried out under anhydrous conditions in the presence of a solvent which is inert to the strong base. Amides such as dimethylformamide and dimethylacetamide are particularly useful.

The N-oxides of the present invention are easily prepared in the usual way, by simple oxidation of the pyridazine. Usually an oxidation is carried out at the last step in the synthetic procedure. The usual oxidizing agents for such processes are organic peroxy acids, of which peroxybenzoic acid and the chloroperoxybenzoic acids are typical. Oxidations are carried out readily near the ambient temperature, for example, at the reflux temperature of a reaction mixture in a halogenated alkane solvent such as dichloromethane and the like.

In general, it is advisable to use excess amounts of the relatively inexpensive reactants in the above process steps, to assure that the more expensive or harder to obtain reactants are fully utilized. As the examples below illustrate, excess amounts in the range of from about 10% to about 100%, or even up to several hundred percent, can beneficially be used when the economics of the process justify doing so.

The following preparative examples further illustrate the synthesis of the present compounds, and assure that the reader can obtain any desired compound.

Preparation 1

3,6-dichloro-4-(1-hydroxymethyl-1-methylethyl)-pyridazine

To a 5-liter flask were added 341 g. of 2,2-dimethyl-1,3-propanediol, 500 ml. of water, 223 g. of 3,6-dichloropyridazine, 100 ml. of sulfuric acid in 900 ml. of water and 51 g. of silver nitrate. To the mixture was then added, dropwise, with an insulating mantle around the flask, 600 g. of ammonium persulfate dissolved in 1 liter of water. The addition was carried out in about 20 minutes, while the temperature rose from 33° to 86°. When the addition was complete, the insulating mantle was removed and the flask was placed in a water bath to cool it. When the temperature had reached 40°, 1200 ml. of dichloromethane was added and the mixture was stirred for 10 minutes more and filtered through a polypropylene filter pad. The solids were washed with 500 ml. of dichloromethane, and the layers of the combined filtrate were separated. The aqueous layer was extracted with 1 liter of dichloromethane, and the combined organic layers were extracted with 1 liter of water, and dried over sodium sulfate. The solvent was removed under vacuum, to leave 385 g. of a gummy solid. Most of the solid was removed and dissolved in 1200 ml. of toluene at 85°. It was then cooled to 0° and filtered, and the solids were washed with cold toluene and dried under vacuum to obtain 152 g. of the desired intermediate product, 97% pure by nuclear magnetic resonance analysis, m.p. 133°–136°.

Preparation 1A

3,6-dichloro-4-(1-hydroxymethyl-1-methylethyl)-pyridazine

Ten ml. of water and 0.33 ml. of sulfuric acid were heated to 80°, and to it were added 0.75 g. of 3,6-dichloropyridazine and 2.55 g. of 3-hydroxy-2,2-dimethylpropanaldehyde. Then a solution of 5.7 g. of ammonium persulfate in 15 ml. of water was added dropwise over 10 minutes. The temperature of the mixture reached 100° during the addition. The mixture was stirred for one hour, and then 0.51 g. of the aldehyde and 1.1 g. of ammonium persulfate were added, and the mixture was stirred one hour more at 90°. It was then cooled and extracted twice with 30 ml. portions of dichloromethane. The organic layers were combined, washed with 30 ml. of water and then with 30 ml. of saturated aqueous sodium bicarbonate, and dried with sodium sulfate. The solvent was removed under vacuum to obtain 1.38 g. of oil, which was chromatographed on 100 g. of silica gel, eluting with one liter of 3:7 ethyl acetate:hexane and then with 2:3 ethyl acetate:hexane. The product-containing fractions were combined and evaporated under vacuum to obtain 0.43 g. of the desired product in crude form, about 80% pure by nuclear magnetic resonance analysis. The spectrum, taken in $CDCl_3$ on a 90 mmHz instrument, showed the following characteristic features: $\delta$7.59 (s, 1H); 4.02 (broad s, 3H); 1.46 (s, 6H).

Preparation 2

3,6-dichloro-4-(1-hydroxymethyl-1-methylethyl)-pyridazine

To a 500 ml. flask were added 22.2 g. of 2,2-dimethyl-1,3-propanediol, 100 ml. of water, 14.9 g. of 3,6-dichloropyridazine and 9.2 ml. of trifluoroacetic acid. The mixture was heated to 37° and 17.0 g. of silver nitrate was added. To the mixture was then added 39.9 g. of ammonium persulfate, dissolved in 75 ml. of water, over 8 minutes. The temperature increased as soon as the addition began, the ultimately reached 80°. The mixture was then cooled to ambient temperature, and 100 ml. of dichloromethane was added. It was stirred for 5 minutes and filtered, and the solids were washed with 50 ml. of dichloromethane, which was added to the filtrate. The layers of the filtrate were separated, and the aqueous layer was washed with 100 ml. of dichloromethane. The organic layers were combined and washed twice with 100 ml. portions of water. The organic layer was then dried with sodium sulfate and evaporated under vacuum. The tacky residue was dissolved in 50 ml. of toluene at 95° and filtered while still hot. The solution was cooled to 0° and filtered, and the solids were washed with cold toluene and vacuum dried to obtain 13.0 g. of the desired intermediate. The filtrate was concentrated under vacuum and was chromatographed on silica gel with 40% ethyl acetate in hexane to obtain 3.6 g. of additional product.

The silver salts which had been recovered in the first filtration step were washed with methanol and vacuum dried to obtain 10.6 g. of silver salts. The aqueous layer from the first filtrate was treated with ammonium chloride, and the resulting precipitate was filtered and dried to obtain 2.3 g. of additional silver salt.

EXAMPLE 1

3,6-dichloro-4-(1-chloromethyl-1-methylethyl)pyridazine

A 140 g. portion of the above intermediate was slurried in 660 ml. of dry toluene, and 61 ml. of dry pyridine was added. To the mixture was added, over a period of 7 minutes, 55.5 ml. of thionyl chloride. The temperature increased to 55°, and a condenser was placed on the vessel and the mixture was heated to and held at 75° for 10 hours. The mixture was then allowed to cool, with stirring, over 6 hours. An additional 6.1 ml. portion of pyridine and 5.5 ml. of thionyl chloride were added, and the mixture was heated again to 75° and stirred at that temperature for 14 hours. It was then cooled, and 300 ml. of 1N hydrochloric acid was added. The mixture warmed to 45°, and was stirred until it reached ambient temperature again. The organic layer was separated, and was washed with two 300 ml. portions of water and then with 300 ml. of brine. It was then dried over sodium sulfate and evaporated under vacuum to a thick oil. The oil crystallized upon cooling, and was dried further without heating to remove remaining toluene. It was then recrystallized by adding it to 300 ml. of boiling isopropanol, and cooling the solution to ambient temperature over 1 hour, with scratching. The mixture was filtered, and the filter cake was washed twice with 50 ml. portions of cold isopropanol and was vacuum dried to obtain 108.6 g. of the desired product, m.p. 66.5°-68.5°. Further concentration and crystallization of the isopropanol produced 13.4 g. of additional product. The combined product was analyzed by high performance liquid chromatography against an authentic standard, with 3:2 methanol:water as the eluant on a Zorbax ODS column, using ultraviolet detection at 254 nm. The product was indicated to be 100% pure. Its elemental analysis was as follows.

Theory: C, 40.11; H, 3.79; N, 11.43; Found: C, 39.88; H, 3.52; N, 11.43.

EXAMPLE 2

3,6-dichloro-4-(1-bromomethyl-1-methylethyl)pyridazine

A 22.1 g. portion of the product of Preparation 1 was dissolved in 65 ml. of pyridine, and was added over a period of 15 minutes to a slurry of 21 g. of p-toluenesulfonyl chloride in 10 ml. of pyridine. The temperature dropped to 18° at first, and then rose to 30°. The mixture was stirred at ambient temperature for 16 hours, and then 100 ml. of dichloromethane was added and the mixture was cooled to 0°. To it was added 70 ml. of concentrated hydrochloric acid, while the temperature was held below 30°. The layers were separated, and the aqueous layer was extracted with 100 ml. of dichloromethane. The organic layers were combined and washed twice with 100 ml. portions of water and then with 100 ml. of brine. The organic layer was then dried with magnesium sulfate, and was evaporated to dryness under vacuum to obtain 34.9 g. of a solid. Five g. of the solids were removed, and the rest was recrystallized from 120 ml. of boiling isopropanol to obtain 26.3 g. of white 3,6-dichloro-4-(1-p-toluenesulfonyloxymethyl-1-methylethyl)pyridazine, m.p. 110°-113°.

A 37.5 g. portion of the above intermediate, obtained by successive reactions, was combined with 13.9 g. of lithium bromide in 100 ml. of dry dimethylsulfoxide under nitrogen, and the mixture was heated to 110° and stirred at that temperature for 2 hours. The mixture was then cooled to ambient temperature, and 100 ml. of water was added dropwise. When one-half of the water had been added, 10 mg. of crystals of the desired product was added, as seeds. When all of the water was in, the mixture was stirred until the temperature fell to 25°, and an additional 15 minutes. The mixture was then filtered, and the filter cake was washed three times with 50 ml. portions of water, and was vacuum dried to obtain 27.7 g. of solid. It was recrystallized by adding it to 55 ml. of boiling isopropanol and cooling to 0°. The mixture was filtered and the solids were washed with cold isopropanol to obtain 25.9 g. of dry product, m.p. 86.5°–88.5°. Its elemental analysis was as follows.

Theory: C, 33.84; H, 3.19; N, 9.86; Cl, 24.97; Br, 28.14; Found: C, 33.89; H, 3.10; N, 9.80; Cl, 25.43; Br, 29.12.

EXAMPLE 3

3,6-dichloro-4-(1-fluoromethyl-1-methylethyl)pyridazine

Fifteen g. of the product of Preparation 1 was dissolved in 450 ml. of dichloromethane and 13.8 g. of triethylamine, and the solution was cooled to 5° under nitrogen. To it was added 16.5 g. of diethylaminosulfur trifluoride, in small portions. A mild exotherm resulted but the temperature did not rise above 10°. The mixture was then stirred at 5° for 3.5 hours, and was slowly added to 400 ml. of cold water. Sodium bicarbonate was added until the aqueous layer was neutral, and the organic layer was then separated and washed with 200 ml. of 1N hydrochloric acid and 100 ml. of brine. It was then dried over magnesium sulfate, and evaporated under vacuum to an oil. The oil was dissolved in 50 ml. of dichloromethane, and the solution was filtered through 50 ml. of silica gel. The filtrate was evaporated under vacuum to a pasty solid, which was purified by high performance liquid chromatography, eluting with 9:1 heptane:ethyl acetate. The product-containing fractions were combined and evaporated under vacuum, and the residue was rechromatographed in the same manner to obtain about 70 mg. of the desired product, m.p. 36°–38°. The product's identity was confirmed by nuclear magnetic resonance analysis on a 60-mHz instrument in $CDCl_3$, which revealed the following features: $\delta$1.53 (d, 6H, J=2 Hz, gem-$CH_3$); 4.65 (d, 2H, J=47 Hz, —$CH_2F$); 7.43 (S, 1H, aromatic).

Preparation 3

3,6-dichloro-4-(1-ethyl-1-hydroxymethylpropyl)pyridazine

Twenty g. of 3,6-dichloropyridazine, 2.3 g. of silver nitrate and 44.4 g. of 2,2-diethyl-1,3-propanediol were slurried in 280 ml. of water and 19.7 g. of sulfuric acid. To the mixture were added, simultaneously, solutions of 61.3 g. of ammonium persulfate in 200 ml. of water and 20 g. of silver nitrate in 40 ml. of water, over a period of 20 minutes at 55°. The mixture heated exothermically to 70°, and it was cooled to ambient temperature after the addition was complete. The aqueous layer was then decanted off, and the solids remaining were slurried twice in 800 ml. of diethyl ether. The resulting solution was shaken with the aqueous layer, and the layers were separated again. The aqueous layer was then made basic to pH 9 with ammonium hydroxide, and was re-extracted with 500 ml. of diethyl ether. The ether was evaporated under vacuum to obtain 46 g. of brown oil, which was purified by high performance liquid chromatography, eluting with 6:1 heptane:ethyl acetate. The product-containing fractions were combined and evaporated under vacuum to obtain, after recrystallization from diethyl ether/heptane, 0.54 g. of the desired product, m.p. 85°–87°.

EXAMPLE 4

3,6-dichloro-4-(1-chloromethyl-1-ethylpropyl)pyridazine

A 1.3 g. portion of the product of Preparation 3 was collected by concentrating the impure fractions from the chromatography above, mixed with an equal amount of a byproduct, 4-chloro-6,6-diethylpyridazino[3,4-b]furan. It was combined with 1.9 g. of thionyl chloride and 1.2 g. of pyridine in 40 ml. of toluene, and the mixture was stirred at 73° for 18 hours. An additional 1.2 g. of pyridine and 1.9 g. of thionyl chloride were added, and the mixture was stirred at 73° for 2.5 hours more. It was then evaporated under vacuum to a semi-solid, and was dissolved in 150 ml. of diethyl ether and 70 ml. of 1N hydrochloric acid. The organic layer was separated, and was washed with brine and dried over magnesium sulfate. It was then evaporated under vacuum to obtain 1.2 g. of oil, which was chromatographed over 100 ml. of silica gel, eluting with 6:1 heptane:ethyl acetate. The product-containing fractions were combined, and the impure product was rechromatographed over 50 ml. of silica gel, eluting with 9:1 heptane:ethyl acetate to obtain 270 mg. of the desired product, m.p. 45°–47°. Its elemental analysis was as follows.

Theory: C, 44.89; H, 4.90; N, 10.47; Found: C, 44.86; H, 4.69; N, 10.48.

Preparation 4

3,6-dichloro-4-(1-hydroxymethyl-1-methylbutyl)pyridazine

Twenty g. of 3,6-dichloropyridazine was alkylated with 44.4 g. of 2-methyl-2-propyl-1,3-propanediol, following the process of Preparation 3 above. In this case the chromatography was run with 3:1 heptane:ethyl acetate as the eluant, and the residue from evaporation of the combined product-containing fractions was recrystallized from diethyl ether/heptane to obtain 0.43 g. of the desired intermediate product, m.p. 99°–100°.

EXAMPLE 5

3,6-dichloro-4-(1-chloromethyl-1-methylbutyl)pyridazine

One g. of the product of Preparation 4, obtained from successive reactions, was dissolved in 25 ml. of toluene and 0.95 g. of pyridine. To the solution was added 1.43 g. of thionyl chloride dissolved in 10 ml. of toluene, dropwise, over 10 minutes at ambient temperature. The mixture was then stirred at 75° for 20 hours, and was then cooled and evaporated under vacuum. The pasty residue was dissolved in 150 ml. of diethyl ether and 70 ml. of water, and the organic layer was separated. It was washed with 50 ml. of water, and with 50 ml. of brine, and was dried over magnesium sulfate and evaporated under vacuum to obtain 1.2 g. of oil. It was chromatographed over 50 ml. of silica gel, eluting with 9:1 heptane:ethyl acetate. The product-containing fractions were combined and evaporated to obtain 0.42 g. of the desired product, m.p. 68°–69°. Its elemental analysis was as follows.

Theory: C, 44.89; H, 4.90; N, 10.47; Found: C, 45.10; H, 4.66; N, 10.45.

Preparation 5

3,6-dichloro-4-isopropylpyridazine

Fifty g. of 3,6-dichloropyridazine was slurried in 500 ml. of water with 28.5 g. of silver nitrate and 66.5 g. of isobutyric acid at 50°. Five hundred ml. of water and 98.6 g. of sulfuric acid were added, and the mixture was heated to 60°. To it was added 228 g. of ammonium persulfate, dissolved in 500 ml. of water. The mixture warmed to 75° as the persulfate was slowly added, and after the addition the mixture was cooled to 10° and ice was added to it. The pH was then adjusted to 9-10 with ammonium hydroxide, and the mixture was extracted three times with 400 ml. portions of diethyl ether. The organic layers were combined and washed twice with 400 ml. portions of 0.5N sodium hydroxide. The organic layer was then washed with brine, dried over magnesium sulfate, and evaporated under vacuum to obtain 52 g. of impure product. It was chromatographed by high performance liquid chromatography, eluting with 5:1 hexane:ethyl acetate, and the desired product was obtained as an oil, amounting to 25 g.

EXAMPLE 6

3,6-dichloro-4-(1-chloromethylethyl)pyridazine

Five g. of the product of Preparation 5 was combined with 3.5 g. of sulfuryl chloride and 25 mg. of benzoyl peroxide in 25 ml. of carbon tetrachloride at ambient temperature under nitrogen, and a 250-watt infrared reflector light was placed close to the flask. The mixture was stirred with irradiation for 3.5 hours, by which time it had warmed to 62° from the lamp. The mixture was then evaporated under vacuum to an oil, which was purified by chromatography on a high performance preparative instrument, eluting with 9:1 hexane:ethyl acetate. Evaporation of the product-containing fractions gave 0.70 g. of the desired product. Its elemental analysis was as follows.

Theory: C, 37.28; H, 3.13; N, 12.42; Found: C, 37.07; H, 3.04; N, 12.15.

Preparation 6

3,6-dichloro-4-t-butylpyridazine

A 375 g. portion of 3,6-dichloropyridazine was slurried with 578 g. of pivalic acid in 367 g. of sulfuric acid and 1500 ml. of water, and the mixture was warmed to 40°. Then 48.2 g. of silver nitrate was added, and the mixture was heated to 62°. To it was added 1 kg. of ammonium persulfate in 2 liters of water over a period of 1 hour. The temperature rose exothermically, and was controlled at 80° maximum. After the addition, the mixture was stirred for 15 minutes, and was then cooled to 15° with an ice-water bath. The mixture was then cooled further by the addition of ice, and its pH was adjusted to 9 with ammonium hydroxide. It was then stirred vigorously for 1 hour, while gummy material was scraped from the sides of the vessel as needed. It was then filtered, and the solids were washed with 2 liters of water and dried on the filter pad. The solids were then slurried in 5 liters of diethyl ether and the slurry was filtered. The filtrate was washed three times with 500 ml. portions of 1N sodium hydroxide, and the washes were combined and extracted with 500 ml. of diethyl ether. That ether was combined with the first ether filtrate, and was washed with 500 ml. of brine. The organic layer was dried over magnesium sulfate and carbon treated at the reflux temperature. It was then cooled and filtered through diatomaceous earth, and the filtrate was evaporated under vacuum to obtain 449 g. of the desired intermediate.

EXAMPLE 7

3,6-dichloro-4-[1,1-bis(chloromethyl)-2-chloroethyl]-pyridazine

A 5.5 g. portion of the product of Example 1 was combined with 9.3 g. of sulfuryl chloride and 10 mg. of benzoyl peroxide in 15 ml. of carbon tetrachloride, and the mixture was irradiated with an infrared lamp as described above in Example 6. Stirring and irradiation was continued for 96 hours at about 40°, and additional sulfuryl chloride was added from time to time, until a total of 37.2 g. was added. After the 96 hours, the mixture was evaporated under vacuum to obtain 6.3 g. of oil, which was purified by high performance liquid chromatography. The product-containing fractions were combined with similar fractions from another batch, and that mixture was purified again by chromatography, eluting with 10:1 heptane:ethyl acetate, to obtain 0.23 g. of the desired product, m.p. 111°-112°. The elemental analysis was as follows.

Theory: C, 31.15; H, 2.29; N, 9.08; Cl, 57.47; Found: C, 31.00; H, 2.22; N, 9.35; Cl, 57.67.

EXAMPLE 8

3,6-dichloro-4-(1-chloromethyl-2-chloro-1-methylethyl)pyridazine

Two g. of the product of Preparation 6 above was combined with 2.6 g. of sulfuryl chloride and 50 mg. of benzoyl peroxide in 2.5 ml. of carbon tetrachloride, and the mixture was stirred with irradiation from a 250-watt infrared reflector lamp for 2 hours. Then 0.66 g. of additional sulfuryl chloride was added, and the reaction was continued for another 2 hours. The mixture was then evaporated under vacuum to obtain 2.3 g. of oil, which was chromtographed by high performance liquid chromatography, eluting with 9:1 heptane:ethyl acetate. About 0.9 g. of the desired product in impure form was collected, and was re-chromatographed with 19:1 heptane:ethyl acetate. About 0.6 g. of impure product was obtained, which was re-treated with 0.67 g. of sulfuryl chloride and benzoyl peroxide, with irradiation as before. The mixture was treated under the lamp at 60° for 20 minutes, and was then set in the freezer overnight. It was then evaporated to a colorless oil under vacuum, and the oil was chromatographed by high performance liquid chromatography, eluting with dichloromethane, to obtain 100 mg. of the desired product, m.p. 92°-94°. The elemental analysis was as follows.

Theory: C, 35.07; H, 2.94; N, 10.22; Found: C, 35.34; H, 3.00; N, 10.48.

EXAMPLE 9

3,6-dichloro-4-(1-chloromethyl-2,2-dichloro-1-methylethyl)pyridazine

Fifty g. of the product of Preparation 6 above was combined with 99 g. of sulfuryl chloride and 25 mg. of benzoyl peroxide in 125 ml. of carbon tetrachloride, and the mixture was irradiated with an infrared lamp as described in the examples above. After 20 hours, an additional 99 g. of sulfuryl chloride was added, and irradiation was continued for 7 hours more. The temperature of the reaction mixture was in the range 58°-61° during the process. It was then cooled and evaporated to dryness under vacuum, and the resulting oil was purified by high performance liquid chromatography, eluting with 10:1 heptane:ethyl acetate, to obtain 1.76 g. of the desired product, m.p. 82°-85°. Its elemental analysis was as follows.

Theory: C, 31.15; H, 2.29; N, 9.08; Cl, 57.47; Found: C, 31.23; H, 2.26; N, 9.28; Cl, 57.73.

EXAMPLE 10

3,6-dichloro-4-(1-iodomethyl-1-methylethyl)pyridazine

A 10.3 g. portion of the product of Preparation 6 was combined with 11.25 g. of N-iodosuccinimide and 100 mg. of benzoyl peroxide in 500 ml. of carbon tetrachloride, and the mixture was irradiated with a 250-watt infrared lamp about 15 cm. from the Pyrex flask. The mixture was stirred under gentle reflux for about 1.25 hours, and then 10 drops of sulfuryl chloride were added. After 2.25 hours, 20 drops more of sulfuryl chloride were added, and reflux was continued. After 4.5 hours, a second lamp of the same type was also placed 15 cm. from the flask. After 7.25 hours, another 5 g. of N-iodosuccinimide was added and reaction was continued for a total of 25 hours, when the mixture was cooled and filtered. The filtrate was concentrated under vacuum to 20.9 g. of oily residue, which was chromatographed on 200 g. of silica gel, eluting with hexane:-diethyl ether. The initial ratio of the solvents was 50:1, changing to 6:1 and finally to 1:1. The product-containing fractions were combined and concentrated, and the residue was crystallized from diethyl ether/heptane to obtain 0.65 g. of product, m.p. 104°-106°. Rechromatography of the mother liquor gave about 1 g. of crystalline product, which was combined with the first crop and recrystallized to obtain 1.1 g. of pale yellow needles, m.p. 106°-108°. The elemental analysis was as follows.

Theory: C, 29.03; H, 2.74; N, 8.46; Found: C, 29.26; H, 2.80; N, 8.25.

EXAMPLE 11

3,6-dichloro-4-(1-chloromethyl-1-methylethyl)-5-methylpyridazine

Ten g. of the product of Example 1 was slurried with 120 ml. of water, 10 g. of acetic acid, 6.1 g. of sulfuric acid and 3.6 g. of silver nitrate, and the mixture was heated to 60°. To it was added a solution of 28.6 g. of ammonium persulfate in 50 ml. of water. The reaction was exothermic, and the temperature reached 84° upon addition of the first small amount of persulfate. The mixture was then cooled to 60° and the rest of the persulfate was added over 20 minutes, holding the temperature at 60°-65°. After the addition, the mixture was stirred for 1 hour while it cooled to ambient temperature, and it was then chilled to 10° and its pH was adjusted to 7-8 with ammonium hydroxide. It was then allowed to stand, and the clear aqueous supernatant was poured off. The remaining material was slurried twice with 200 ml. portions of diethyl ether. The ether was combined with the aqueous layer, and shaken, and the layers were separated. The aqueous layer was re-extracted with 200 ml. of additional diethyl ether, and all of the organic layers were combined and washed with 100 ml. of brine and dried over magnesium sulfate. The solvent was then removed under vacuum, leaving an oil which appeared, under nuclear magnetic resonance analysis, to be mainly starting material.

The oil was combined with 10 g. of acetic acid, 3.6 g. of silver nitrate and 6.1 g. of sulfuric acid in 70 ml. of water, and 28.6 g. of ammonium persulfate in 60 ml. of water was slowly added, as above. When the addition was complete, the mixture was cooled to 40°, and additional portions of the same amounts of acetic acid, silver nitrate and ammonium persulfate were added. The mixture was stirred for 1 hour more, and was worked up as described in the first step of this example. About 6 g. of oil was obtained, which was separated by high performance liquid chromatography, eluting with 5:1 heptane:ethyl acetate. The product-containing fractions were combined, and the residue of them was re-chromatographed, eluting this time with 9:1 heptane:ethyl acetate to obtain 0.53 g. of the desired product, m.p. 56°-58°. Its elemental analysis was as follows.

Theory: C, 42.63; H, 4.37; N, 11.05; Found: C, 42.93; H, 4.51; N, 10.93.

EXAMPLE 12

3-chloro-4-(1-chloromethyl-1-methylethyl)-6-(furan-2-ylmethoxy)pyridazine

A 0.66 g. portion of 50% sodium hydride in mineral oil was washed with hexane, 40 ml. of anhydrous dimethylformamide was added, and the suspension was cooled to 10°. To it was added 1.47 g. of furan-2-ylmethanol, and the mixture was warmed and stirred at ambient temperature for 1.5 hours. Then 3.0 g. of the product of Example 1 was added over a period of 5 minutes, dissolved in 5 ml. of anhydrous dimethylformamide. The mixture was warmed to 45° exothermically, and it was then heated to 60° and stirred at that temperature for 1.5 hours. Then it was cooled and stirred at ambient temperature for 16 hours, and was evaporated under vacuum to a dark oil. The oil was slurried in 300 ml. of water, and the aqueous mixture was extracted with 200 ml. of ethyl acetate. The organic layer was separated, washed with 50 ml. of brine and dried over magnesium sulfate. The solvent was then removed under vacuum to obtain 2.8 g. of oil, which was chromatographed by high performance liquid chromatography, eluting with dichloromethane, to obtain 1.15 g. of impure product. It was re-chromatographed, eluting with 5:1 hexane:ethyl acetate, to obtain 300 mg. of the desired product, the elemental analysis of which was as follows.

Theory: C, 51.85; H, 4.69; N, 9.30; Found: C, 51.63; H, 4.56; N, 9.31.

EXAMPLE 13

3,6-dichloro-4-(1-chloromethyl-1-methylethyl)pyridazine, $N^2$-oxide

EXAMPLE 14

3,6-dichloro-4-(1-chloromethyl-1-methylethyl)pyridazine, $N^1$-oxide

Six g. of the compound of Example 1 was slurried in 50 ml. of dichloromethane, and 8 g. of 3-chloroperoxybenzoic acid was added. The mixture was stirred at the reflux temperature for 8 hours, and was then evaporated under vacuum to a solid. It was taken up in a minimum amount of carbon tetrachloride:ethyl acetate, and poured over 300 ml. of silica gel. Elution of the column with 2:1 heptane:ethyl acetate produced about 6 g. of an impure mixture of both oxides. The mixture was separated by high performance liquid chromatography, eluting with 5:1 heptane:ethyl acetate. About 0.4 g. of the compound of Example 13 was obtained, m.p. 90°–92°. Its elemental analysis was as follows.

Theory: C, 37.60; H, 3.55; N, 10.96; Found: C, 37.88; H, 3.65; N, 11.21.

The chromatography also separated about 0.4 g. of the product of Example 14, m.p. 106°–107°.

Theory: C, 37.60; H, 3.55; N, 10.96; Found: C, 37.72; H, 3.33; N, 10.70.

Preparation 7

3,6-dibromopyridazine

A 22.8 g. portion of 3,6-dioxopyridazine (maleic acid hydrazide) was combined with 115 g. of phosphorus oxybromide and 150 ml. of benzene and the mixture was stirred for 3 hours at 70°–80°. It was cooled and diluted with 100 ml. of diethyl ether, and the mixture was poured over ice and made slightly basic with ammonium hydroxide. The organic layer was separated, and was washed with water and dried over sodium sulfate. It was then concentrated under vacuum, and the white residue was recrystallized from cyclohexane to obtain 6.4 g. of the desired intermediate, m.p. 116°–117°.

Theory: C, 20.28; H, 0.85; N, 11.78; Found: C, 20.44; H, 0.86; N, 11.81.

EXAMPLE 15

3,6-dibromo-4-(1-bromomethyl-1-methylethyl)pyridazine

Three g. of 3,6-dibromopyridazine, 1 g. of silver nitrate, 3.2 g. of 2,2-dimethyl-1,3-propanediol, 7 ml. of water and 1.9 g. of concentrated sulfuric acid were stirred at 30° while 5.8 g. of ammonium persulfate dissolved in 15 ml. of water was added dropwise. The temperature rose to 60°. The mixture was then cooled and extracted with 100 ml. of dichloromethane. The organic layer was washed with 10 ml. of water and dried over magnesium sulfate. The solvent was removed under vacuum, and the resulting solid was chromatographed on silica gel, eluting with 3:1 hexane:ethyl acetate in a high performance liquid chromatography device. The product-containing fractions were combined and evaporated under vacuum, and the product was recrystallized from benzene/hexane to obtain 1.4 g. of 3,6-dibromo-4-(1-hydroxymethyl-1-methylethyl)-pyridazine m.p. 140°–141°.

A 9.3 g. portion of the above intermediate, obtained from successive reactions, was stirred with 20 ml. of pyridine and 8.6 g. of p-toluenesulfonyl chloride at ambient temperature overnight. The mixture was then poured into ice-water, diethyl ether was added, and the resulting precipitate was collected. The solids were dissolved in ethyl acetate, and the solution was washed with 0.5N hydrochloric acid and then with aqueous sodium bicarbonate. The organic layer was dried over magnesium sulfate, and was evaporated under vacuum. The solids were recrystallized from ethyl acetate/hexane to obtain 10 g. of 3,6-dibromo-4-(1-methyl-p-toluenesulfonyloxymethylethyl)pyridazine, m.p. 119°–121°.

To 4.6 g. of the above intermediate was added 10 ml. of dimethylsulfoxide and 1.7 g. of lithium bromide. The mixture was stirred at 110° for 2.5 hours, and it was then cooled and poured into ice-water. The resulting white gummy solid was dissolved in diethyl ether, and the solution was washed with water and dried. The solvent was removed under vacuum to leave an oil, which was purified by high-performance liquid chromatography over silica gel, eluting with 4:1 heptane:ethyl acetate. About 600 mg. of product, m.p. 125°–126°, was collected.

Theory: C, 25.77; H, 2.43; N, 7.51: Found: C, 26.02; H, 2.30; N, 7.53.

EXAMPLE 16

3-bromo-6-chloro-4-(1-chloromethyl-1-methylethyl)-pyridazine

Four g. of 3,6-dibromo-4-(1-methyl-p-toluenesulfonyloxymethylethyl)pyridazine was combined with 8 ml. of dimethylsulfoxide and 1.5 g. of lithium chloride and the mixture was stirred for 2 hours at 90°–100°. It was then poured into ice-water, and the white solid was collected and dissolved in diethyl ether. The solution was washed with water, dried, and evaporated under vacuum. The residue was recrystallized from hexane to obtain about 2.1 g. of the desired product, m.p. 79°–81°. Its nuclear magnetic resonance spectrum, run in CDCl3 on a 60 mHz instrument, showed characteristic features at δ1.65, s, 6H, 4.10, s, 2H; 7.45, s, 1H.

Preparation 8

3,6-dimethylpyridazine

Fifty g. of 2,5-dimethylfuran was combined with 156 g. of anhydrous sodium carbonate and 1,050 ml. of methanol and the mixture was chilled to −15°. To it was added, over 45 minutes, 83.1 g. of bromine while the temperature was held constant. The mixture was then stirred while it warmed to ambient temperature, and the liquid portion was decanted into a 4-liter separatory funnel containing 2 liters of brine. The liquid was extracted twice with 800 ml. portions of dichloromethane, and the organic layers were combined and washed with 100 ml. of fresh brine. Then the organic portion was dried over magnesium sulfate, filtered and evaporated under vacuum to obtain an oily residue which was vacuum distilled at 45°–48°, at 8–11 mm. pressure, to obtain 49 g. of 2,5-dimethoxy-2,5-dimethylfuran.

A 54 g. portion of the above intermediate, obtained by successive reactions, was combined with 68 ml. of 1% aqueous acetic acid, and then 18.5 ml. of 85% hydrazine hydrate was added over a period of 25 minutes. The temperature of the mixture increased to 65° while the addition was made, and the mixture was then heated to 78° and stirred overnight at that temperature. It was then cooled and filtered. The filtrate was evaporated under vacuum to obtain a brown oil, which was distilled. The product remained in the distillation vessel, and was purified by high-performance liquid chromatography, eluting with ethyl acetate, to obtain 16.3 g. of 3,6-dimethylpyridazine.

EXAMPLE 17

4-(1-chloromethyl-1-methylethyl)-3,6-dimethylpyridazine

A 23.9 g. portion of 2,2-dimethyl-1,3-propanediol, 88 ml. of water, 11.3 g. of 3,6-dimethylpyridazine, 3.6 g. of silver nitrate and 12.3 g. of concentrated sulfuric acid were combined at ambient temperature, and to the mixture was added 41.8 g. of ammonium persulfate dissolved in 68 ml. of water. The addition was dropwise over a period of only 15 minutes. The reaction temperature rose to 75°, and the mixture was stirred at that temperature for 30 minutes. The reaction mixture was then worked up substantially as described in the examples above to obtain 1.2 g. of 4-(1-hydroxymethyl-1-methylethyl)-3,6-dimethylpyridazine.

A 2.2 g. portion of the above intermediate, obtained from successive reactions, was reacted with 3.5 g. of p-toluenesulfonyl chloride in 40 ml. of dry pyridine, and the mixture was worked up substantially as described in Example 15 above to obtain 2.6 g. of 3,6-dimethyl-1-(1-methyl-1-p-toluenesulfonyloxymethylethyl)pyridazine, m.p. 121°–122°.

One g. of the above intermediate was dissolved in 10 ml. of dimethylsulfoxide, and 0.5 g. of lithium chloride was added. The mixture was heated to 110° and held at that temperature for 2 hours. It was then cooled to about 40°, and poured into 300 ml. of water. The mixture was salted out with sodium chloride, and was extracted twice with 150 ml. portions of diethyl ether. The organics were evaporated under vacuum, and the resulting oil was slurried in 10 ml. of water and extracted with 200 ml. of warm heptane. The organic layer was then filtered through phase separation paper, and was evaporated under vacuum to obtain 0.35 g. of an oil, which crystallized on standing. It was then dissolved in ethyl acetate and poured over silica gel and evaporated again to obtain 0.21 g. of the desired product, m.p. 57°–59°.

Theory: C, 60.45; H, 7.61; N, 14.10; Found: C, 60.74; H, 7.40; N, 14.02.

EXAMPLE 18

4-(1-bromomethyl-1-methylethyl)-3,6-dimethylpyridazine

A 1.0 g. portion of 3,6-dimethyl-1-(1-methyl-1-p-toluenesulfonyloxymethylethyl)pyridazine was dissolved in 10 ml. of dimethylsulfoxide under nitrogen, and 0.52 g. of lithium bromide was added. The mixture was held at 110° for 2.5 hours, and was poured into 300 ml. of water, which was then saturated with sodium chloride. The solution was extracted twice with 150 ml. portions of diethyl ether, and the combined organic layers were washed with brine and dried over magnesium sulfate. The organic solution was then evaporated under vacuum to obtain a residue of impure product, which was recrystallized from diethyl ether/heptane to obtain 0.43 g. of the desired product, m.p. 45°–46°.

Theory: C, 49.40; H, 6.22; N, 11.52; Found: C, 49.66; H, 5.96; N, 11.61.

EXAMPLE 19

3,6-dichloro-4-(chloromethyl)dimethylsilylpyridazine

Twenty g. of 3,6-dichloropyridazine was combined with 50 ml. of nitrogen-bubbled acetonitrile, 29.2 g. of (chloromethyl)dimethylsilane and 39.2 g. of di-t-butylperoxide. The mixture was kept under nitrogen, and was exposed overnight to a 275 watt infrared lamp. The final temperature was 44°. The lamp was then moved closer, and the temperature increased to 54° while irradiation continued for 5 hours more. The mixture was then evaporated under vacuum, and the residue was dissolved in 100 ml. of boiling carbon tetrachloride and the solution was filtered. The filtrate was then subjected to high-performance liquid chromatography, eluting with 7:1 heptane:ethyl acetate, and the product-containing fractions were combined to obtain 231 mg. of the desired product as an oil. Analysis by mass spectroscopy showed the desired molecular ion of weight 254, and the expected ion of weight 205, resulting from loss of the chloromethyl group in the analysis.

Preparation 9

3-chloro-6-cyanopyridazine

Ninety g. of 6-oxo-3-pyridazinecarboxylic acid was slurried with 270 ml. of phosphorus oxychloride and 1 ml. of dimethylformamide under nitrogen, and the mixture was stirred under reflux for 1.5 hours. It was then evaporated under vacuum, and the residue was poured into 3 liters of 28% aqueous ammonia. The aqueous mixture was then poured into a 22 liter flask, and was extracted three times with 4-liter portions of ethyl acetate. After the first extraction, the pH was adjusted to 7 with hydrochloric acid. The extracts were combined and evaporated under vacuum to obtain 27.7 g. of 3-chloro-6-pyridazinecarboxamide.

The above intermediate was slurried with 300 ml. of phosphorus oxychloride under nitrogen, and the mixture was held at 80°–90° for 2.5 hours. It was then evaporated under vacuum, and the residue was slowly added to 800 ml. of warm water. The aqueous mixture was extracted twice with 800 ml. portions of ethyl acetate, and then was extracted three times with 800 ml. portions of diethyl ether. All of the organic layers were combined, and washed with brine. The washed organic layer was dried over magnesium sulfate and evaporated under vacuum. The residue was taken up in diethyl ether and poured over 600 ml. of silica gel, eluting with diethyl ether. The product-containing fractions were collected and evaporated under vacuum to obtain 13 g. of the desired intermediate.

EXAMPLE 20

3-chloro-4-(1-chloromethyl-1-methylethyl)-6-cyanopyridazine

EXAMPLE 21

3-chloro-4-[1,1-bis(chloromethyl)ethyl]-6-cyanopyridazine

Five g. of 3-chloro-6-cyanopyridazine was combined with 8 g. of pivalic acid, 1.2 g. of silver nitrate, 5.26 g. of concentrated sulfuric acid and 20 ml. of water, and the mixture was heated to 60°. A 14.3 g. portion of ammonium persulfate was dissolved in 28 ml. of water, and the solution was added to the first mixture over 15 minutes, while the temperature was held between 60°–75°. Then the mixture was heated to 80° for 20 minutes, and was chilled to 15° and its pH was adjusted to 9 with ammonium hydroxide. The water layer was then removed, and the remaining solids were washed three times with 200 ml. portions of diethyl ether. The ether was added to the water layer, and the organic extract was separated. The water layer was extracted again with diethyl ether, and all of the organics were combined and washed twice with 100 ml. portions of 1N sodium hydroxide. The organic layer was then washed with brine and dried over magnesium sulfate. It was then evaporated under vacuum and purified by high-performance liquid chromatography, eluting with 6:1 heptane:ethyl acetate to obtain 2.7 g. of 3chloro-4-t-butyl-6-cyanopyridazine, m.p. 118°–119°.

The above intermediate was added to 10 ml. of carbon tetrachloride and 1.9 g. of sulfuryl chloride under nitrogen at ambient temperature. The mixture was irradiated with a 275 watt sun lamp for about 15 minutes. The temperature of the mixture reached 55°. The mixture was then evaporated under vacuum, and the residue was purified by high-performance liquid chromatography, eluting with 10:1 heptane:ethyl acetate. The product-containing fractions were combined and evaporated under vacuum to obtain 0.87 g. of the product of Example 20, m.p. 75°–76°.

Theory: C, 46.98; H, 3.94; N, 18.26; Found: C, 47.07; H, 3.80; N, 18.00.

The fractions which came off before those containing the product above were combined and evaporated to obtain 100 mg. of the product of Example 21, m.p. 66°–68°.

EXAMPLE 22

3,6-dichloro-4-(2-chlorocyclohexyl)pyridazine

A 17.9 g. portion of 3,6-dichloropyridazine was combined with 120 ml. of cyclohexane, 4.1 g. of silver nitrate, 11 ml. of concentrated sulfuric acid and 60 ml. of acetonitrile in 120 ml. of water at 50°. To that mixture was then added 41.1 g. of ammonium persulfate dissolved in 60 ml. of water, in 5 minutes. The mixture was stirred for 2 hours more, and was then diluted with 300 ml. of dichloromethane and filtered. The filtrate was extracted three times with 300 ml. portions of dichloromethane, and the combined organics were washed with 50 ml. of saturated aqueous sodium bicarbonate and 50 ml. of water. The organic layer was then filtered through phase separation paper and concentrated under vacuum to obtain 31.7 g. of tan solid. The residue was crystallized from ethyl acetate to obtain 11.5 g. of 3,6-dichloro-4-(2-hydroxycyclohexyl)pyridazine, m.p. 141°–143°. A second crop of 6.6 g. of product, m.p. 139°–140°, was also collected.

Five g. of the above first-crop intermediate was added to 5 ml. of pyridine, 50 ml. of toluene and 4.5 ml. of thionyl chloride, and the mixture was stirred for 2 hours at 80°. It was then cooled and diluted with 100 ml. of water, and was extracted three times with 150 ml. portions of diethyl ether. The combined organics were washed with 25 ml. portions of saturated aqueous sodium bicarbonate and water. The organic layer was then dried over magnesium sulfate and evaporated under vacuum. The resulting oil was filtered through 15 g. of silica gel with 100 ml. of diethyl ether and was crystallized. A total of 1.8 g. of product, m.p. 93°–95°, was collected in two crystallizations.

Theory: C, 45.23; H, 4.18; N, 10.55: Found: C, 44.99; H, 3.93; N, 10.62.

Preparation 10

3chloro-6-methylpyridazine

A 245 g. portion of levulinic acid was added to 3 liters of ethanol and 69 g. of anhydrous hydrazine was added. The mixture was stirred under reflux for 3 hours, and the solvent was removed under vacuum. The residue was slurried with 400 ml. of ethyl acetate and the solids were separated by filtration to obtain 259 g. of 3-methyl-4,5-dihydro-6-oxopyridazine.

The above intermediate was added to 2.5 liters of acetic acid and the mixture was heated with stirring to 100° and was held at 100°–114° while 338 g. of bromine was added over a period of 30 minutes. It was stirred under reflux for 1 hour after the addition, and then it was cooled and evaporated under vacuum, and 1.5 liters of water was added. The mixture was filtered, and the filtrate was chilled and was filtered again to obtain a total of 202 g. of 3-methyl-6-oxopyridazine.

The above intermediate was slowly added to 1,280 ml. of phosphorus oxychloride, and the mixture was slowly heated to the reflux temperature and held at that temperature for 1 hour. It was then evaporated under vacuum, and the oily residue was added to water with stirring. The pH was adjusted to 6, and the aqueous mixture was extracted with dichloromethane. The extract was washed with brine, was dried and was evaporated under vacuum. The aqueous layer was re-adjusted to pH 6 and was extracted two times with 1,500 ml. portions of dichloromethane. The extracts were combined, washed with brine, dried and evaporated under vacuum to obtain a total of 1.5 g. of 3-chloro-6-methylpyridazine.

EXAMPLE 23

3-chloro-4-(1-chloromethyl-1-methylethyl)-6-methylpyridazine

Ten g. of 3-chloro-6-methylpyridazine was combined with 17.8 g. of 2,2-dimethyl-1-3-propanediol, 6.6 g. of silver nitrate, 9.2 g. of concentrated sulfuric acid and 120 ml. of water, and the mixture was warmed to 29°. To it was added, dropwise, 31.1 g. of ammonium persulfate dissolved in 90 ml. of water. The temperature was 65° at the end of the 15-minute addition. The mixture was stirred at about that temperature for 20 minutes more, and was then cooled to ambient temperature and was extracted with dichloromethane. The extract was washed with water and evaporated under vacuum. The residue was recrystallized from 80 ml. of toluene and then from 100 ml. of dichloromethane. A total of 3.9 g. of 3-chloro-4-(1-hydroxymethyl-1-methylethyl)-6-methylpyridazine was obtained, m.p. 151°–153°.

A 1.5 g. portion of the above intermediate was reacted with 2.2 g. of p-toluenesulfonyl chloride under nitrogen at ambient temperature in pyridine, as described in examples above, to obtain 1.6 g. of 3-chloro-4-(1-methyl-1-p-toluenesulfonyloxymethylethyl)-6-methylpyridazine.

One g. of the above intermediate was dissolved in 10 ml. of dimethylsulfoxide and was reacted with 0.24 g. of lithium chloride at 110°, and was worked up as described in the examples above to obtain 0.42 g. of the desired product, m.p. 41°–42°.

Theory: C, 49.33; H, 5.62; N, 12.78; Found: C, 49.55; H, 5.79; N, 12.56.

EXAMPLE 24

4-(1-bromomethyl-1-methylethyl)-3-chloro-6-methylpyridazine

A 0.6 g. portion of 3-chloro-4-(1-methyl-1-p-toluenesulfonyloxymethylethyl)-6-methylpyridazine was dissolved in 10 ml. of dimethylsulfoxide and was reacted with 0.3 g. of lithium bromide at 110°, as described in examples above, to obtain 200 mg. of the desired product, a light yellow oil, the identity of which was confirmed by mass spectroscopy. A molecular ion of weight 262 was observed, as was the ion of weight 169 which resulted from loss of the bromomethyl group from the compound.

EXAMPLE 25

3,6-dichloro-4-(2,2-dichloro-1-methylcyclopropyl)-pyridazine

A 3.5 g. portion of 3,6-dichloropyridazine was slurried with 4.0 g. of 2,2-dichloro-1-methylcyclopropanecarboxylic acid, 15 ml. of water, 3.4 g. of concentrated sulfuric acid in 20 ml. of water, and 4.0 g. of silver nitrate, and the mixture was heated to 65° with rapid stirring. To it was added 11.9 g. of ammonium persulfate in 20 ml. of water, over 20 minutes, while the temperature was held at 70°-76°. The mixture was stirred 15 minutes after the addition and cooled to 10°. Its pH was adjusted to 8.0 with ammonium hydroxide, and the water layer was then decanted off. The remaining solids were washed twice with 100 ml. portions of diethyl ether, and that ether was then used to extract the water layer. The organic layer was washed with 1N sodium hydroxide and with brine, and dried. The solvent was removed under vacuum, and the residue was purified by chromatography, eluting with 3:1 heptane:ethyl acetate. The product-containing fractions were combined and evaporated, and the residue was recrystallized from heptane, to obtain 0.52 g. of the desired product, m.p. 78°-79°.

Theory: C, 35.33; H, 2.22; N, 10.30; Found: C, 35.16; H, 2.21; N, 10.24.

Greenhouse Tests

Representative compounds of the invention have been tested in standardized systems to determine the range of their efficacy against plant pathogens. The following reports are illustrative.

Formulations of the compounds are identified by their formula letters used below, at the end of the specification.

Test I

The test compounds were formulated for application by dissolving 48 mg. of a selected compound in 1.2 ml. of solvent. The solvent was prepared by mixing 100 ml. of "TWEEN 20" (a nonionic surfactant) with 500 ml. of acetone and 500 ml. of ethanol. The solvent/compound solution was finally diluted to 120 ml. with deionized water; the solution was further diluted for some tests to obtain the concentrations shown in the table below.

The formulated test compounds were applied to the foliage of squash plants for the control of *Pseudoperonospora cubensis*, the causative organism of downy mildew. The formulated test compounds were sprayed by hand in a fume hood. Single pots of plants were placed on raised, revolving pedestals in the hood. Using a spray gun, all test solutions were applied by hand at 40 psi. As the spray was delivered, the pedestals were rotated to expose all plant surfaces to the spray pattern and the spray was applied to the run-off point. All treatments were allowed to dry and the host plants were inoculated with the pathogen 2 to 4 hours later.

The effectiveness of test compounds in controlling the disease was rated on a scale of 1 to 9, as follows:
1. 0–19% control
2. 20–29%
3. 30–39%
4. 40–59%
5. 60–74%
6. 75–89%
7. 90–96%
8. 97–99%
9. 100% control, no disease Also a phytotoxicity rating was recorded, where phytotoxicity was present, using a scale from 1 to 5 with 1 indicating no toxicity and 5 indicating death to the plant. Finally, when phytotoxicity was present, a letter rating was given to the plant indicating the type of injury caused to the plant. These injuries were coded as follows:
G=General necrosis
W=Wilting
S=Stunting
C=Chlorosis
F=Formative Table I presents the activity of typical compounds of the present invention when evaluated in the method described above. Repeated tests at a given application rate have sometimes been performed; in such cases, representative results are given.

TABLE I

| Compound of Example No. | Concentration | Result |
|---|---|---|
| 1 | 400 ppm | 9 |
|   | 100 | 9 |
|   | 100 | 8 |
|   | 25 | 9 |
|   | 25 | 8 |
|   | 6.25 | 6 |
| 2 | 400 | 9 |
|   | 100 | 9 |
|   | 25 | 8 |
|   | 6.25 | 3 |
|   | 6.25 | 8 |
|   | 1.56 | 1 |
| 3 | 400 | 9 |
|   | 100 | 9 |
|   | 25 | 3 |
| 4 | 400 | 7 2 G |
|   | 100 | 3 |
|   | 25 | 1 |
| 5 | 400 | 8 2 G |
|   | 100 | 5 |
|   | 25 | 2 |
| 6 | 400 | 9 |
|   | 100 | 8 |
|   | 100 | 9 |
|   | 25 | 1 |
|   | 25 | 3 |
|   | 6.25 | 1 |
| 7 | 400 | 9 2 C |
|   | 100 | 5 |
|   | 25 | 1 |
| 8 | 400 | 8 2 G |
|   | 400 | 9 2 C |
|   | 100 | 9 |
|   | 100 | 8 |
|   | 25 | 8 |
|   | 6.25 | 1 |
| 9 | 400 | 8 |
|   | 100 | 3 |
|   | 25 | 1 |
| 10 | 400 | 9 |
|   | 100 | 9 |
|   | 25 | 8 |
|   | 6.25 | 2 |
| 11 | 400 | 8 2 G |
|   |   | 3 C |
|   | 100 | 7 2 C |
|   | 25 | 3 |
| 12 | 400 | 8 |
|   | 100 | 7 |
|   | 25 | 2 |
| 13 | 400 | 5 |
|   | 100 | 4 |
|   | 25 | 2 |
| 14 | 400 | 9 |
|   | 100 | 7 |
|   | 25 | 4 |
| 15 | 400 | 9 |
|   | 100 | 8 |
|   | 25 | 8 |
|   | 6.25 | 4 |
| 16 | 400 | 9 |
|   | 100 | 9 |
|   | 25 | 8 |
|   | 6.25 | 4 |
| 17 | 400 | 9 |
|   | 100 | 8 |
|   | 25 | 3 |
|   | 6.25 | 2 |

TABLE I-continued

| Compound of Example No. | Concentration | Result |
|---|---|---|
| 18 | 400 | 9 |
|  | 100 | 8 |
|  | 25 | 4 |
|  | 6.25 | 2 |
| 19 | 400 | 1 |
| 20 | 400 | 9 |
|  | 100 | 1 |
|  | 25 | 1 |
| 21 | 400 | 9 |
|  | 100 | 3 |
|  | 25 | 1 |
| 22 | 400 | 9 |
|  | 100 | 7 |
|  | 25 | 2 |
| 23 | 400 | 9 |
|  | 100 | 8 |
|  | 25 | 1 |
| 24 | 400 | 8 |
|  | 100 | 5 |
|  | 25 | 1 |

Test II

The compound of Example 1 was tested against downy mildew (*Pseudoperonospora cubensis*) of cucumber, evaluating the effects of rain and of delayed inoculation of the disease. The compounds were formulated substantially as described in Test I, and were applied at three rates, as shown below, to 18-day-old MR17 cucumber plants. When the applications had dried on the foliage of the plants, some plants were given 0.5 inch of artificial rain. Some plants were inoculated 2 hours after application of the compounds, and others were inoculated 72 hours after treatment. After inoculation, the plants were held in a moist chamber for 24 hours, and then were held in a greenhouse for 72 hours. They were then observed with the following results. The effectiveness of the test compound was rated on the 1-9 scale.

TABLE II

|  | 2 Hours | | 72 Hours | |
|---|---|---|---|---|
| Concentration | Rain | No Rain | Rain | No Rain |
| 1 ppm | 1 | 1 | | |
| 5 ppm | 5 | 9 | 1 | 1 |
| 10 | 7 | 9 | 1 | 1 |
| 20 | 9 | 9 | 1 | 1 |

Similar tests were carried out with formulations of the compounds of Examples 1 and 2. The first disease inoculations were made 2 to 4 hours after treatment; other plants were inoculated two days after treatment. The formulations are indicated by their identifying letters in the Compositions section of this document.

TABLE IIa

| Cpd. of Ex. No. | Form. | Rate | 2-4 Hours | | 48 Hours | |
|---|---|---|---|---|---|---|
|  |  |  | Rain | No Rain | Rain | No Rain |
| 1 | 2EC,K | 1 ppm | 1 | 1 | 1 | 1 |
|  |  | 3 | 8 | 8 |  |  |
|  | 50WP,P | 1 | 1 | 1 | 1 | 1 |
|  |  | 3 | 1 | 4 |  |  |
| 2 | 1AS,C | 10 |  | 9 |  |  |
|  | 1EC,G | 1 |  | 4 |  |  |
|  |  | 3 |  | 9 |  |  |

Test III

The compound of Example 1 was tested against blue mold (*Peronospora tabacina*) of tobacco by applying aqueous dispersions of the compound, prepared as described in Test I above, to tobacco seedlings infected with blue mold. The seedlings were grown in 18-inch-square flats, and the test plots were prepared by dividing the flats into strips 2.5 inches wide. Three replicate strips were sprayed with each of three concentrations of the compound of Example 1, and were compared to solvent-treated and to untreated control strips. When the formulations had been applied and had dried overnight in the greenhouse, the pathogen was grown out by exposing the flats first to a mist room for 24 hours, then to a greenhouse for 10 days, and finally to a mist room for 24 hours more. The disease was then observed, using an 0-10 scale, which is an expansion of the 1-9 scale explained above, where 0 indicates no control and 10 indicates complete control.

Treatments at 400 ppm. of the compound averaged 9.8; the 100 ppm. treatments were rated 10 in all replicates; and 50 ppm. treatments averaged 9.6.

Test IV

The compounds of Examples 1 and 2 were tested against *Aphanomyces euteiches* root rot of peas. The compounds were applied to Progress No. 9 pea seed by spraying 25 g. of seed in a tumbling mixer with 2 ml. of acetone containing the proper amount of compound to provide the rates shown below. Six treated seeds were planted in each 3-inch plastic pot in sterilized greenhouse soil, and each pot was drenched with 10 ml. of *A. euteiches* zoospore suspension. The pots were held in the dark at 21° until the plants emerged, and were then held in a greenhouse for six weeks, and then observed. The results were as follows.

TABLE IV

| Compound of Example No. | Rate | Disease Control | Crop Injury |
|---|---|---|---|
| 1 | 0.1 g./kg | 8% | 25% |
|  | 1 | 27 |  |
|  | 5 | 100 |  |
| 2 | 0.1 | 0 |  |
|  | 1 | 50 |  |
|  | 5 | 100 |  |

Test V

In this test, compounds were applied to pea plants as soil drenches for the control of Aphanomyces root rot. The compounds were formulated substantially as described in Test I above, and each 3-inch pot of 13-day-old Progress No. 9 pea plants was drenched with 25 ml. of aqueous dispersion. Some pots were treated with 20 ppm. dispersion, providing 1 lb./A. of compound, and others were treated with 100 ppm. dispersion, providing 5 lb./A. of compound. The following day, each pot was inoculated with 10 ml. of *A. euteiches* zoospore suspension. The plants were then held for 48 hours at 21° in the dark, and were then held in the greenhouse for 12-14 days.

TABLE V

| Compound of Example No. | Rate | Percent Control |
|---|---|---|
| 1 | 1 lb./A. | 0% |
|  | 5 | 17 |
| 2 | 1 | 0 |
|  | 5 | 1 |

Test VI

The compound of Example 1 was formulated as an emulsifiable concentrate containing 1 pound of compound per gallon, formula M below, and was tested against black shank of tobacco (*Phytophthora parasitica* var. *nicotiniae*). The emulsifiable concentrate was diluted to provide the concentrations shown in the table below, and the foliage of tobacco plants grown in plastic pots was sprayed with the emulsions. Only five leaves of each plant were sprayed, and the stems of the plants were wrapped with cotton so that the emulsion could not contact the stems. Other pots of tobacco were treated by soil drench application, by pouring 25 ml. of emulsion into each pot. After the plants had been treated and the foliage of the sprayed plants had dried, each plant was inoculated with black shank by piercing a hole in the stem, and putting a plug of the black shank pathogen, grown on agar, into the puncture wound and sealing the wound with lanolin. The plants were grown in the greenhouse for a week, and were observed, using the 0–10 scale.

TABLE VI

| Rate | Foliar Spray | Soil Drench |
| --- | --- | --- |
| 400 ppm. | 0 | 10 |
| 200 | 0 | 10 |
| 100 | 0 | 10 |
| 50 | 0 | — |

Test VII

The compounds of Examples 1 and 2 were tested, applied as soil drenches, for the control of tobacco black shank. The compounds were applied to the 4-inch square pots in 40 ml. of aqueous dispersion, formulated substantially as described in Test I above. Each pot contained one healthy tobacco plant. The day after the compounds were applied, each plant was inoculated with *Phytophthora parasitica* as described in Test VI above. The plants were rated on the 1–9 scale 1 week and 2 weeks after treatment. Four weeks after treatment, the plants were pulled up, their stems were split, and the length of stem affected by black shank was measured. Two plants constituted each treatment, and the results of the two plants were averaged to prepare the following table.

TABLE VII

| Compound of Example No. | Rate | 1 Week | 2 Weeks | 4 Weeks |
| --- | --- | --- | --- | --- |
| 1 | 0.25 lb./A. | 8.8 | 8.5 | 5.7 cm. |
|  | 0.5 | 8.5 | 8.5 | 0 |
|  | 1 | 9 | 9 | 0 |
|  | 2 | 9 | 9 | 0 |
| 2 | 0.25 | 6.8 | 6.5 | 1.2 |
|  | 0.5 | 8 | 7.5 | 6.2 |
|  | 1 | 8 | 7.8 | 0 |
|  | 2 | 8.5 | 8.5 | 0.4 |
| Control |  | 3 | 1 | 19.6 |

Test VIII

This test was carried out in the same manner as was Test VII above, except that the compounds were applied to the 4-inch pots in only 20 ml. of aqueous dispersion. The plants were observed only once, 1 week after treatment.

TABLE VIII

| Compound of Example No. | Rate | Disease Control |
| --- | --- | --- |
| 1 | 0.12 lb./A. | 1 |
|  | 0.25 | 5 |
|  | 0.5 | 9 |
| 2 | 0.12 | 1 |
|  | 0.25 | 1 |
|  | 0.5 | 9 |

Test IX

The compound of Example 1 was tested against tobacco black shank by both foliar and soil drench application methods. The compound was supplied as an emulsifiable concentrate containing 1 pound of compound per gallon, formula M below, and was diluted with water to provide the concentrations in the table below. About 25 ml. of emulsion was applied to the foliage of each tobacco plant in the foliar application experiment, and the same amount was poured over the soil of each pot in the soil drench portion of the experiment. Three replicate pots of each treatment were used. Some plants were inoculated with tobacco black shank, as described in Test VI above, immediately before treatment, and others were inoculated 1 and 4 days after treatment. The plants were observed 11 days after treatment, using the 1–9 scale.

TABLE IX

|  | Foliar | | | Soil Drench | | |
| --- | --- | --- | --- | --- | --- | --- |
| Concentration | 0 Day | 1 Day | 4 Day | 0 Day | 1 Day | 4 Day |
| 6.25 ppm | 1 | 1 | 1 | 6 | 1 | 6 |
| 12.5 | 1 | 1 | 1 | 6 | 6 | 8 |
| 25 | 6 | 1 | 1 | 8 | 9 | 9 |
| 50 | 9 | 9 | 9 | 9 | 9 | 9 |
| 100 | 9 | 9 | 9 | 9 | 9 | 9 |

Test X

The compounds of Examples 1 and 2 were tested against late blight of tomato, in tests where the compounds were applied to the foliage of Rutgers tomato plants. The compounds were formulated substantially as described in Test I above, and enough of the aqueous dispersion was sprayed on each plant to wet all of the leaf surfaces. The plants were inoculated with a suspension of zoospores of *Phytophthora infestans*, immediately after the treatments had dried, or on the third, fifth or seventh day thereafter as shown in the table below. The 7-day delayed plants received a light mist of rain before inoculation, because of a leak in the greenhouse roof. After the plants were inoculated, they were held in a moist chamber for 24 hours, and then transferred to a greenhouse. The injury caused by the late blight was read on the 1–9 scale, about 2 weeks after treatment.

TABLE X

| Compound of Example No. | Conc. | 0 Day | 3 Day | 5 Day | 7 Day |
| --- | --- | --- | --- | --- | --- |
| 1 | 25 ppm | 6 |  |  |  |
|  | 50 | 9 | 1 | 1 | 1 |
|  | 100 | 9 | 1 | 1 | 1 |
|  | 400 | 9 | 5 | 1 | 1 |
| 2 | 25 | 6 |  |  |  |
|  | 50 | 9 | 1 | 1 | 1 |
|  | 100 | 9 | 1 | 1 | 1 |
|  | 400 | 9 | 8.5 | 8.5 | 1 |

Similar tests were carried out with formulations of the compound of Example 1.

TABLE Xa

| Form. | Rate | 0 Day | 2 Days |
|---|---|---|---|
| 2EC,M | 50 ppm | 4 | 4 |
|  | 400 | 9 | 8.5 |
| 2EC,J | 100 | 8 | 4 |
| 1AS,C | 100 | 8.5 | 1 |
|  | 400 | 9 | 6 |
| 1AS,E | 50 | 8 | 1 |
|  | 400 | 8.5 | 8 |

Test XI

Compounds of the invention were applied to tomato plants for the control of late blight in a test which was carried out essentially as was that of Test X, except that the plants were all inoculated on the same day as the treatment, and the disease was observed 5 days thereafter. Tests with the compound of Example 1 were rated on the 0–10 scale.

TABLE XI

| Concentration | Disease Control |
|---|---|
| 50 ppm | 4.5 |
| 100 | 9.2 |

Tests with other compounds were rated on the 1–9 scale.

| Cpd. of Ex. No. | Concentration | Disease Control |
|---|---|---|
| 15 | 100 | 7.5 |
|  | 50 | 6.0 |
|  | 25 | 3.0 |
|  | 12.5 | 2.0 |
| 16 | 400 | 9.0 |
|  | 100 | 9.0 |
|  | 25 | 8.5 |
| 20 | 100 | 1.0 |
| 21 | 400 | 5.0 |
|  | 100 | 4.0 |
|  | 50 | 4.0 |
| 23 | 400 | 7.0 |
|  | 100 | 4.0 |
|  | 50 | 1.0 |
| 24 | 100 | 7.0 |
|  | 50 | 1.0 |

Test XII

Compounds were applied to 3-inch plastic pots, each containing two 20-day-old tomato plants, for the control of late blight. The compounds were formulated substantially as described in Test I above, and 25 ml. of aqueous dispersion was applied to each pot. The day after application of the compounds, all of the plants were inoculated by spraying a suspension of *Phytophthora infestans* over the foliage, and the plants were then held in a moist chamber for 1 day. The plants were then transferred to a greenhouse, and the disease was observed about 4 weeks after treatment. Observations were rated on the 1–9 scale.

TABLE XII

| Compound of Example No. | Rate | Disease Control |
|---|---|---|
| 1 | 0.5 lb./A. | 5 |
|  | 1.0 | 7 |
|  | 2.0 | 9 |
| 2 | 0.5 | 1 |
|  | 1.0 | 5 |
|  | 2.0 | 7 |

Test XIII

The compound of Example 1 was tested in a number of formulations for the control of late blight of tomato. The formulations were diluted in tap water to provide the concentrations shown in the table below, and the dispersions were sprayed over all of the surfaces of the foliage of tomato plants growing in plastic pots. Some plants were inoculated with late blight as soon as the treatments had dried, and others were inoculated two days thereafter. After inoculation, the plants were held for a day in a moist chamber, and were then transferred to a greenhouse. Disease control was observed and rated on the 1–9 scale about 2 weeks after treatment.

TABLE XIII

| Formulation | Rate | 0 Day | 2 Days |
|---|---|---|---|
| 1 lb./gal. EC[1], M | 50 | 4 | 4 |
|  | 100 | 4 | 5 |
|  | 400 | 9 2G | 8.5 2G |
| 2 lb./gal. EC, J | 50 | 7 | 1 |
|  | 100 | 8 | 7 |
|  | 400 | 8 | 7 |
| 1 lb/gal. AS, [2]D | 50 | 8 | 1 |
|  | 100 | 8 | 4 |
|  | 400 | 8.5 3G | 8 3G |
| 1 lb./gal. AS, E | 50 | 6 | 1 |
|  | 100 | 8 | 1 |
|  | 400 | 8.5 3G | 8 3G |
| 1 lb./gal. AS, C | 50 | 8 | 1 |
|  | 100 | 8.5 | 1 |
|  | 400 | 9 2G | 6 2G |

[1]Emulsifiable concentrate
[2]Aqueous suspension

Test XIV

The compounds of Examples 1 and 2 were applied to pea seed and tested for the control of *Pythium aphanidermatum* damping-off. The proper amount of compound for each treatment was dissolved in 2 ml. of acetone and sprayed on 25 g. of tumbling seed in a small drum mixer. The seeds were allowed to dry, and six seeds were planted in each 2.5-inch round plastic pot of Pythium-infested soil. The pots were kept in the dark until the plants emerged, and were then transferred to the greenhouse and evaluated 11 days after planting. Each treatment group consisted of two replicate pots, which were averaged to prepare the table below.

TABLE XIV

| Compound of Example No. | Rate | Live Plants | Disease Control |
|---|---|---|---|
| 1 | 0.1 g./kg. | 0 | 0% |
|  | 1.0 | 4.5 | 89 |
|  | 5.0 | 4 | 78 |
| 2 | 0.1 | 1 | 10 |
|  | 1.0 | 4.5 | 89 |
|  | 5.0 | 6 | 100 |

Test XV

Four-inch square pots of Penncross bent grass were treated with compounds of this invention, formulated substantially as described in Test I above, at the rates shown in the table below. The day after the grass was treated, each pot was inoculated with three 5 mm. plugs of *P. aphanidermatum* culture, growing on potato dextrose agar. The pots were then placed in a moist chamber for 3 days at 26°, and the disease was then read, on the 1-9 scale.

TABLE XV

| Compound of Example No. | Rate | Disease Control |
|---|---|---|
| 1 | 1.5 lb./A. | 8.5 |
| 1 | 3 | 8 |
| 1 | 6 | 9 |
| 2 | 1.5 | 8.5 |
| 2 | 3 | 5 |
| 2 | 6 | 1 |

Test XVI

This test was carried out substantially as was Test XV above, except that, when the pots had been sprayed with the test compound dispersions, the grass was washed with 20 ml. of water per pot to carry the dispersion off the grass and into the soil.

TABLE XVI

| Compound of Example No. | Rate | Disease Control |
|---|---|---|
| 1 | 1.5 lb./A. | 1 |
| 1 | 3 | 7 |
| 1 | 6 | 9 |
| 2 | 1.5 | 1 |
| 2 | 3 | 3 |
| 2 | 6 | 7 |

Test XVII

Cotton seed was sprayed with the proper amounts of the compounds named in the table below to give the named dosages; 2 ml. of acetone was used to dissolve the correct amount of compound for each 25-gram portion of seed. After the acetone had evaporated, 10 seeds were planted in each 2.5-inch round plastic pot containing Pythium-infested soil. Three replicate pots were used for each treatment. The pots were held in the dark at 21° until the plants emerged, and they were then transferred to a greenhouse and held until the plants were evaluated at 11 days after planting. The replicates were averaged to prepare the following table.

TABLE XVII

| Compound of Example No. | Rate | Crop Stand | Disease Control |
|---|---|---|---|
| 1 | 0.1 g./kg. | 3.7 | 75% |
| | 1.0 | 7.0 | 84 |
| | 2.0 | 5.0 | 80 |
| 2 | 0.1 | 2.3 | 65 |
| | 1.0 | 5.3 | 81 |
| | 2.0 | 7.3 | 84 |

Test XVIII

In this test, cotton seed was planted, 10 seeds per pot in Pythium-infested soil, and the test compounds were applied to the pots as soil drenches. The compounds were formulated substantially as described in Test I above, and were diluted up so that 25 ml. of dispersion was applied to each pot. The pots were held and evaluated as described in Test XVII above.

TABLE XVIII

| Compound of Example No. | Rate | Crop Stand | Disease Control |
|---|---|---|---|
| 1 | 0.5 lb./A. | 3.0 | 71% |
| | 1.0 | 6.0 | 82 |
| | 2.0 | 6.7 | 83 |
| 2 | 0.5 | 1.7 | 55 |
| | 1.0 | 4.7 | 79 |
| | 2.0 | 3.7 | 75 |

Test XIX

In this test, the compound of Example 1 was soil-drenched on pots in which cotton and soybean seeds were planted in Pythium-infested soil. In each 2.5-inch round pot, six soybean or twelve cotton seeds were planted, and the compounds, formulated substantially as described in Test I and diluted up to 10 ml. of aqueous dispersion per pot, were poured over the soil. The pots were held in a moist chamber until the plants had emerged, when the test was evaluated. Each treatment group consisted of three replicate pots, which were averaged to prepare the following table.

TABLE XIX

| | Cotton | | Soybean | |
|---|---|---|---|---|
| Rate | Crop Stand | Disease Control | Crop Stand | Disease Control |
| 2.5 lb./A. | 6 | 9.7 | 5.7 | 10 |
| 5.0 | 7.7 | 9.8 | 6 | 10 |
| 10.0 | 6.7 | 9.7 | 5.7 | 10 |

Test XX

Compounds were tested to determine their ability to control downy mildew of grape (*Plasmopara viticola*). The compounds were formulated substantially as discussed in Test I, and the aqueous dispersions were sprayed on the foliage of grape plants in pots. Some plants were inoculated with a suspension of *P. viticola* as soon as the spray had dried, and others were inoculated on various days thereafter. The inoculated plants were placed in a moist chamber for five days, then held in a greenhouse for one day, and were put back in the moist chamber for one day more. Then the disease control was read, on the 1-9 scale.

TABLE XX

| Cpd. of Ex. No. | Rate | Disease Control | | | | |
|---|---|---|---|---|---|---|
| | | 0 Day | 1 Day | 3 Days | 5 Days | 7 Days |
| 1 | 50 ppm. | 9 | | 2 | 1 | 1 |
| | 100 | 9 | | 5 | 1 | 1 |
| | 400 | 9 | | 7 | 6 | 2 |
| 2 | 50 | 9 | | 2 | 3 | 1 |
| | 100 | 9 | | 7 | 6 | 2 |
| | 400 | 9 | | 9 | 9 | 5 |
| 15 | 100 | 8 | | | | |
| | 50 | 9 | | | | |
| | 12.5 | 5 | | | | |
| 16 | 400 | 9 | | | | |
| | 100 | 9 | | | | |
| | 25 | 5 | | | | |
| 18 | 100 | 5 | | | | |
| | 12.5 | 5 | | | | |
| 19 | 25 | | 1 | 1 | | |
| | 100 | | 9 | 1 | | |
| 20 | 100 | 1 | | | | |
| 21 | 400 | 7 | | | | |
| | 100 | 7 | | | | |
| | 50 | 1 | | | | |
| 23 | 400 | 9 | | | | |
| | 100 | 5 | | | | |

TABLE XX-continued

| Cpd. of Ex. No. | Rate | Disease Control | | | | |
|---|---|---|---|---|---|---|
| | | 0 Day | 1 Day | 3 Days | 5 Days | 7 Days |
| 24 | 50 | 1 | | | | |
| | 100 | 8 | | | | |
| | 50 | 5 | | | | |
| | 25 | 1 | | | | |

In a variation of the above test, the plants were inoculated 1, 2 or 3 days before the compound was applied. The test in other respects was carried out as above.

| Cpd. of Ex. No. | Rate | 1 Day | 2 Days | 3 Days |
|---|---|---|---|---|
| 19 | 25 ppm | 1.0 | 1.0 | 1.0 |
| | 100 | 1.0 | 1.0 | 1.0 |
| | 400 | 1.0 | 4.0 | 1.0 |

Test XXI

Ruby grape plants growing in plastic pots were inoculated with *P. viticola*, and were placed in moist growing chambers. Three and six days after inoculation, some plants were removed from the chambers and were sprayed with formulations of compounds 1 and 2, prepared substantially as in Test I above. The plants were immediately returned to the moist growing chambers, without allowing the compound sprays to dry. Disease control was observed and rated on the 1-9 scale, on the eighth day after inoculation.

TABLE XXI

| Compound of Example No. | Rate | Disease Control | |
|---|---|---|---|
| | | 3 Days | 6 Days |
| 1 | 50 ppm | 1 | 1 |
| | 100 | 1 | 1 |
| | 400 | 1 | 1 |
| 2 | 50 | 1 | 1 |
| | 100 | 4 | 3 |
| | 400 | 6 | 6 |

Test XXII

The compound of Example 1 was formulated as three different aqueous suspensions containing 1 pound of compound per gallon, and as a 1 lb./gal. and a 2 lb./gal. emulsifiable concentrate. All five formulations were tested, diluted in tap water to provide the concentrations of compounds shown below, against downy mildew of grape. The foliage of the plants was sprayed, and the spray was allowed to dry. Twenty-four hours later, some of the plants were given 0.6 inches of artificial rain. After those plants had dried, about 28 hours after treatment, plants were inoculated with downy mildew. Other plants, which had not been exposed to rain, were inoculated 96 hours after treatment. The disease control obtained was observed and rated on the 1-9 scale about three weeks after treatment with the compound.

TABLE XXII

| Formulation | Rate | 28 Hours | | 96 Hours |
|---|---|---|---|---|
| | | Rain | No Rain | |
| 1 AS, E | 50 ppm | 9 | 9 | 1 |
| | 100 | 8 | 9 | 1 |
| 1 AS, C | 50 | 8 | 6 | 1 |
| | 100 | 8 | 9 | 3 |
| 1 AS, D | 50 | 3 | 9 | 1 |
| | 100 | 9 | 9 | 5 |

TABLE XXII-continued

| Formulation | Rate | 28 Hours | | 96 Hours |
|---|---|---|---|---|
| | | Rain | No Rain | |
| 1 EC, M | 50 | 9 | 9 | 5 |
| | 100 | 9 | 9 | 7 |
| 2 EC, J | 50 | 1 | 9 | 1 |
| | 100 | 8 | 9 | 1 |

Test XXIII

The compounds of Examples 1 and 2 were formulated as 50% wettable powders, and the compound of Example 1 was also formulated as a 2 lb./gal. emulsifiable concentrate. The compound of Example 2 was formulated as a 1 lb./gal. emulsifiable concentrate. All of the formulations were diluted to the concentrations below, and each compound was also tested at the same concentrations in the form of dispersions prepared as described in Test I above. Grape plants were sprayed with the various dilutions, and some of the plants were exposed to 0.5 inch of artificial rain after the sprays had dried. Part of the plants were inoculated with downy mildew 4 hours after treatment, and others were inoculated 72 hours after treatment. The disease control was observed and rated on the 1-9 scale 19 days after treatment.

TABLE XXIII

| Compound of Example No. | Formulation | Rate | 4 Hours | | 72 Hours | |
|---|---|---|---|---|---|---|
| | | | Rain | No Rain | Rain | No Rain |
| 1 | EC, Q | 50 ppm | 9 | 9 | 7 | 1 |
| | | 100 | 9 | 9 | 1 | 8 |
| 1 | WP[1], P | 6.25 | | 1 | | 1 |
| | | 50 | 9 | 9 | 1 | 5 |
| | | 100 | 9 | 9 | 1 | 1 |
| 1 | Test I | 6.25 | | 4 | | 1 |
| | | 50 | 9 | 9 | 1 | 1 |
| | | 100 | 9 | 9 | 1 | 1 |
| 2 | EC, R | 50 | 9 | 8 | 6 | 5 |
| | | 100 | 9 | 9 | 6 | 6 |
| 2 | WP, A | 50 | 9 | 9 | 6 | 8.5 |
| | | 100 | 9 | 9 | 7 | 7 |
| 2 | Test I | 50 | 9 | 9 | 1 | 6 |
| | | 100 | 9 | 9 | 1 | 1 |

Test XXIV

In this test, the compound of Example 2 was formulated as four different 1 lb./gal. aqueous suspensions and as a 1 lb./gal. emulsifiable concentrate, and was tested against downy mildew of grape in the same procedure used in Test XXIII, except that the last inoculation was seven days after treatment, instead of three days.

TABLE XXIV

| Formulation | Rate | 4 Hours | | 7 Days |
|---|---|---|---|---|
| | | Rain | No Rain | |
| AS, F1 | 50 ppm | 9 | 7 | 5 |
| | 100 | 9 | 7 | 7 |
| AS, F2 | 50 | 5 | 7 | 5 |
| | 100 | 9 | 8 | 5 |
| AS, O1 | 50 | 4 | 9 | 5 |
| | 100 | 9 | 9 | 6 |
| AS, O2 | 50 | 9 | 9 | 6 |
| | 100 | 9 | 9 | 7 |
| EC, R | 50 | 9 | 9 | 6 |
| | 100 | 9 | 9 | 8 |

Similar tests with the compounds of Examples 1 and 2 were carried out, in which various formulations of the compounds were used. A number of different inoculation schedules were used as follows.

TABLE XXIVa

| Cpd. of Ex. No. | Form. | Rate ppm. | 0 Day Rain | 0 Day No Rain | 3 Days Rain | 3 Days No Rain | 4 Days |
|---|---|---|---|---|---|---|---|
| 1 | 1EC,M | 12.5 | 7 | 5 | | | |
|   | 2EC,K | 25 | | 9 | | 1 | |
|   | 2EC,J | 50 | 9 | 9 | 7 | 1 | 1 |
|   | 2EC,K | 6.5 | | 4 | | 1 | |
|   | 2EC,K | 100 | | | | | 4 |
| 2 | 1EC,G | 6.25 | | 5 | | 1 | |
|   | 1EC,R | 25 | 9 | 9 | | 1 | |
|   | 1EC,R | 50 | 9 | 8 | | 4 | 1 |
|   | 1EC,R | 100 | 9 | 9 | 6 | 6 | 4 |

Test XXV

The compounds of Examples 1 and 2, formulated as 2 lb./gal. and 1 lb./gal. emulsifiable concentrates K and R, respectively, were tested against downy mildew of grape by spraying the foliage of grape plants with dilutions of the formulations. Two hours and 72 hours after treatment, plants were inoculated with downy mildew, and the plants were incubated in a moist growth chamber until the disease control was read on the tenth day after treatment.

TABLE XXV

| Compound of Example No. | Rate | 2 Hours | 72 Hours |
|---|---|---|---|
| 1 | 12.5 ppm | 5 | 1 |
|   | 25 | 7 | 1 |
|   | 25 | 9 | 5 |
|   | 50 | 9 | 6 |
| 2 | 25 | 9 | 1 |
|   | 50 | 9 | 4 |

Test XXVI

The compound of Example 1 was formulated as a 1 lb./gal. emulsifiable concentrate, formula M below, and diluted to the concentrations shown below. Grape plants were sprayed with the aqueous dispersions, and one plant was inoculated with downy mildew as soon as the spray had dried; another was inoculated 5 days after treatment. Inoculation was accomplished by spraying the lower leaf surfaces only with a suspension of *P. viticola*. The plants were incubated as described in the tests above, and the disease control was read 2 weeks after treatment.

TABLE XXVI

| Rate | 2 Hours | 5 Days |
|---|---|---|
| 50 ppm | 1 | 1 |
| 100 | 7 | 1 |
| 400 | 9 | 2 |

Test XXVII

The compound of Example 1, formulated as 1 lb./gal. emulsifiable concentrate M, was diluted to the rates shown below, and the emulsions were sprayed on the foliage of grape plants. Some of the plants were held in the greenhouse, and others were placed outdoors in hot clear weather, and brought into the greenhouse at night. After periods of time from 0 to 5 days of this treatment, the plants were inoculated with downy mildew, on the undersides of the leaves only. After the inoculation, the plants were held for 2 days in a moist chamber and were then taken to the greenhouse for development of the disease. The plants were read on the 0-10 scale.

TABLE XXVII

| | Greenhouse | | | | Outside | | | |
|---|---|---|---|---|---|---|---|---|
| Rate | 0 Day | 1 Day | 4 Day | 5 Day | 0 Day | 1 Day | 4 Day | 5 Day |
| 125 ppm | 10 | 10 | 10 | 5 | — | 10 | 9.5 | 5 |
| 500 | 10 | 10 | 10 | 9.5 | — | 10 | 10 | 9 |

Test XXVIII

The compound of Example 1 was tested as a seed treatment on squash and soybean seeds for the control of downy mildew. Fifty g. of soybeans and fifty counted squash seeds were placed in a small tumbling drum mixer, and were sprayed with 2 ml. of acetone containing, in one case, 50 mg. of the compound and, in the other test, 5 mg. of the compound. The acetone was allowed to dry off, and the seeds were planted in plastic pots. When the plants emerged, they were infected with downy mildew (*Pseudoperonospora cubensis*) and the disease control was observed and rated on the 0-10 scale. No control of downy mildew on squash was observed. On soybeans, the 5 mg. seed coating gave average control of 6.7, and the 50 mg. seed coat gave an average control of 7.7.

Test XXIX

The compounds of Examples 1, 2 and 10 were formulated substantially as described in Test I above, and the aqueous dispersions were sprayed on the foliage of Golden Crookneck squash plants which were 15 days old at the time of application. The plants were inoculated with downy mildew (*Pseudoperonospora cubensis*). Some plants were inoculated as soon as the treatment had dried, and others were inoculated 24 and 72 hours after treatment. The plants were incubated in a 21° moist chamber for 1 day, and were then held in the greenhouse until they were read, about 2 weeks after treatment. Disease control was rated on the 1-9 scale, and readings of both the cotyledons and the first true leaf of the plants were made.

Test XXIX

| Cpd. of Ex. No. | Rate ppm. | 2 Hours Coty. | 2 Hours 1st Leaf | 24 Hours Coty. | 24 Hours 1st Leaf | 72 Hours Coty. | 72 Hours 1st Leaf |
|---|---|---|---|---|---|---|---|
| 1 | 10 | 9 | 9 | 3 | 1 | | 2 |
|   | 25 | 9 | 9 | 8 | 7 | | 2 |
|   | 50 | 9 | 9 | 9 | 9 | | 2 |
| 2 | 10 | 9 | 9 | 7 | 7 | | 5 |
|   | 25 | 8 | 9 | 9 | 8 | | 4 |
|   | 50 | 9 | 9 | 9 | 9 | | 2 |
| 10 | 10 | 8 | 8 | 1 | 1 | | 2 |
|   | 25 | 9 | 9 | 6 | 2 | | 2 |
|   | 50 | 9 | 9 | 8 | 9 | | 2 |

Test XXX

The compound of Example 1 was formulated substantially as described in Test I above, and the dispersions were sprayed on the outer leaf surfaces of 16-day-old Golden Crookneck squash plants which had been inoculated with downy mildew about 20 hours earlier. The treated plants were allowed to dry, and were then held in a greenhouse for about 2 weeks, when the disease control was rated on the −9 scale. Treatments at 400 ppm. of compound were rated 5; treatments at 100 ppm. were rated 3; and treatments at 25 ppm. were rated 2.

Test XXXI

The compounds of Examples 1 and 2 were formulated substantially as described in Test I above, and were applied to pots in which squash plants were growing. The volume of aqueous dispersion was 25 ml. on each 3-inch plastic pot, and the concentrations were adjusted to provide the dosage rates named below. The plants were inoculated with downy mildew, 24 hours after treatment, and they were then incubated at 21° in a moist chamber for 24 hours. They were then held in a greenhouse for 6 days and the disease control was observed and rated on the 1–9 scale.

TABLE XXXI

| Compound of Example No. | Rate | Disease Control |
|---|---|---|
| 1 | 0.25 lb./A. | 5.5 |
|   | 0.5 | 8 |
|   | 1 | 8.5 |
| 2 | 0.25 | 3.5 |
|   | 0.5 | 8.5 |
|   | 1 | 8.5 |

Test XXXII

The compound of Example 1 was formulated substantially as described in Test I, and was applied to Golden Crookneck squash plants as a spray which covered all of the foliage surfaces. After 2 and 5 days, groups of plants were inoculated with squash downy mildew. The disease control obtained was evaluated by reading the disease on the cotyledons and on the first true leaves separately, using the 1–9 scale.

TABLE XXXII

| Rate | 2 Days | | 5 Days | |
|---|---|---|---|---|
|  | Coty. | 1st Leaf | Coty. | 1st Leaf |
| 100 ppm | 9 | 7 | 5 | 3 |
| 400 | 9 | 9 | — | 8 |

Test XXXIII

The compound of Example 1 was formulated as emulsifiable concentrates, which were diluted to the concentrations shown below and sprayed on all foliar surfaces of Golden Crookneck squash plants. The plants were inoculated with downy mildew as soon as the spray had dried, 2 days thereafter or 5 days thereafter, and the plants were incubated for a day in a moist chamber and then transferred to a greenhouse. The disease control was rated on the 1–9 scale about 3 weeks after treatment.

TABLE XXXIII

| Formulation | Rate | 0 Day | 2 Days | 5 Days |
|---|---|---|---|---|
| 1 lb./gal. | 50 ppm | 9 | 9 | 5 |
| EC, M | 100 | 9 | 9 | 9 |
| 2 lb./gal. | 50 | 9 | 9 | 8 |
| EC, Q | 100 | 9 | 9 | 9 |

Test XXXIV

Various emulsifiable concentrations of compounds 1 and 2 were diluted and sprayed on 13-day-old Golden Crookneck squash plants. Some of the plants were exposed to 0.5 inch of artificial rain as soon as the treatments had dried. Those plants and some of the other treated plants were inoculated with downy mildew 4 hours after treatment, and other plants were inoculated 4 days after treatment. The disease was incubated for 24 hours in a moist chamber, and the plants were then held in a greenhouse for about 2 weeks and were then read on the 1–9 scale.

TABLE XXXIV

| Compound of Example No. | Formulation | Rate | 4 Hours No Rain | 4 Hours Rain | 4 Days |
|---|---|---|---|---|---|
| 1 | 2 lb./gal., K | 10 ppm | 9 | 9 | 6 |
|   |   | 20 | 9 | 9 | 5 |
| 1 | 2 lb./gal., Q | 10 | 9 | 9 | 6 |
|   |   | 20 | 9 | 9 | 5 |
| 2 | 1 lb./gal., G | 10 | 9 | 9 | 8 |
|   |   | 20 | 9 | 9 | 8 |
| 2 | 1 lb./gal., N | 10 | 9 | 9 | 7 |
|   |   | 20 | 9 | 9 | 7.5 |
| 2 | 1 lb./gal., R | 10 | 9 | 9 | 8.5 |
|   |   | 20 | 9 | 9 | 8.5 |

Test XXXV

The compound of Example 1, formulated as a 1 lb./gal. aqueous suspension, as a 1 lb./gal. emulsifiable concentrate, and also in the manner described in Test I, was applied at various concentrations to squash plants. The plants were inoculated with downy mildew as soon as the treatments had dried, and were incubated and grown out as described in the squash downy mildew tests above. Disease control was rated on the 1–10 scale.

TABLE XXXV

| Formulation | Rate | Disease Control |
|---|---|---|
| AS, B | 0.25 ppm | 0 |
|   | 0.5 | 0 |
|   | 1 | 3 |
|   | 6 | 9.5 |
| EC, M | 0.25 | 0 |
|   | 0.5 | 3 |
|   | 1 | 8.6 |
|   | 6 | 10 |
| Test I | 0.25 | 0 |
|   | 0.5 | 0 |
|   | 1 | 0 |
|   | 6 | 7 |

Test XXXVI

Various formulations of the compound of Example 1 were diluted to the concentrations shown below and sprayed over the foliage of 13-day-old squash plants growing in 4-inch plastic pots. Some of the plants were given 0.5 inch of artificial rain on the following day, and were then allowed to air dry. Those plants and some of the other plants were inoculated on the day after treatment, and other plants were inoculated at various times after treatment, with downy mildew. The plants were incubated and held in the greenhouse as described in the squash downy mildew tests above, and were read on the 1–9 scale 6 days after treatment.

TABLE XXXVI

| Formulation | Rate ppm | 1 Day Rain | 1 Day No Rain | 2 Days | 4 Days | 5 Days |
|---|---|---|---|---|---|---|
| 1EC,M | 1 | 3 | 5 | 1 |  |  |
|  | 5 | 8 | 9 | 9 |  |  |
|  | 10 | 8 | 9 | 9 |  |  |

TABLE XXXVI-continued

| Formu-lation. | Rate ppm. | 1 Day Rain | 1 Day No Rain | 2 Days | 4 Days | 5 Days |
|---|---|---|---|---|---|---|
|  | 50 |  | 9 | 9 |  | 5 |
| 2EC,J | 1 | 1 | 5 | 1 |  |  |
|  | 5 | 8 | 9 | 7 |  |  |
|  | 10 | 9 | 9 | 8 |  |  |
| 1AS,D | 1 | 1 | 5 | 1 |  |  |
|  | 5 | 7 | 8 | 5 |  |  |
|  | 10 | 9 | 9 | 7 |  |  |
| 1AS,E | 1 | 1 | 7 | 7 |  |  |
|  | 5 | 8 | 8 | 7 |  |  |
|  | 10 | 8 | 9 | 7 |  |  |
| 1AS,C | 1 | 1 | 8 | 1 |  |  |
|  | 5 | 7 | 9 | 1 |  |  |
|  | 10 | 9 | 9 | 8 |  |  |
| 2EC,K | 20 | 9 | 9 |  | 5 |  |
| 2EC,Q | 50 |  | 9 |  | 9 | 8 |

Test XXXVII

The compound of Example 2, formulated as 1 lb./gal. emulsifiable concentrate R, was diluted to the concentrations shown below and was tested against downy mildew of squash. The plants were sprayed over all of their foliage, and some of the plants were subjected to 0.5 inch of artificial rain as soon as the treatment had dried. As soon as the rain had dried, those plants and other plants were inoculated with downy mildew, and other plants were inoculated 2 days after the treatment. The results, read on the 1-9 scale, were as follows.

TABLE XXXVII

| Rate | 0 Day Rain | 0 Day No Rain | 2 Days |
|---|---|---|---|
| 1 ppm | 6 | 9 | 1 |
| 3 | 9 | 9 | 3 |
| 9 | 9 | 9 | 3 |

Test XXXVIII

The compound of Example 2, formulated as three different emulsifiable concentrates and four different aqueous suspensions, was diluted to the concentrations shown below, and was tested against downy mildew of squash in a test which was carried out exactly as was Test XXXVII above, except for the formulations and the application rates.

TABLE XXXVIII

| Formu-lation | Rate ppm. | 0 Day Rain | 0 Day No Rain | 2 Days | 4 Days |
|---|---|---|---|---|---|
| 1AS, F1 | 1 | 1 | 5 | 1 |  |
|  | 5 | 9 | 9 | 9 |  |
|  | 10 | 9 | 9 | 9 |  |
| 1AS, F2 | 1 | 1 | 5 | 1 |  |
|  | 5 | 7 | 9 | 9 |  |
|  | 10 | 9 | 9 | 9 |  |
| 1AS,O1 | 1 | 1 | 8 | 1 |  |
|  | 5 | 8 | 9 | 5 |  |
|  | 10 | 9 | 9 | 9 |  |
| 1AS,O2 | 1 | 1 | 9 | 4 |  |
|  | 5 | 9 | 9 | 8 |  |
|  | 10 | 9 | 9 | 9 |  |
| 1EC, R | 1 | 1 | 5 | 1 |  |
|  | 5 | 9 | 9 | 8 |  |
|  | 10 | 9 | 9 | 9 |  |
| 1EC, G | 10 | 9 | 9 |  | 8 |
| 1EC, N | 10 | 9 | 9 |  | 7 |
| 1EC, R | 10 | 9 | 9 |  | 8.5 |

Test XXXIX

The compounds named in the table below were formulated substantially as described in Test I and diluted to the named concentrations. Leaves of squash plants were sprayed in a 1.5 cm. wide band across the bottom of the leaf. After the treatment had dried, the edges of the leaf were clipped with scissors to identify the band which was treated. The plant was inoculated with downy mildew, and incubated in such a manner as to encourage development of the disease. Then, the upper side of the leaf was read on the 1-9 scale. The tip of the leaf, above the sprayed band, was called Area A; the opposite side of the leaf from the sprayed band was Area B; and the basal part of the leaf was Area C. The following results were obtained.

TABLE XXXIX

| Compound of Example No. | Rate ppm. | A | B | C |
|---|---|---|---|---|
| 1 | 100 | 9 | 9 | 1 |
|  | 400 | 9 | 9 | 2 |
|  | 1000 | 9 | 9 | 7 |
| 2 | 100 | 8 | 9 | 2 |
|  | 400 | 9 | 9 | 5 |
| 7 | 100 | 1 | 1 | 1 |
|  | 400 | 2 | 7 | 1 |
| 9 | 100 | 1 | 1 | 1 |
|  | 400 | 2 | 3 | 1 |
| 12 | 100 | 1 | 1 | 1 |
|  | 400 | 1 | 4 | 1 |
| 15 | 1000 | 9 | 9 | 5 |
| 19 | 1000 | 1 | 1 | 1 |
| 20 | 500 | 1 | 1 | 1 |
| 23 | 500 | 9 | 9 | 1 |
| 24 | 500 | 9 | 9 | 1 |

Test XL

Lower application rates were used in this test, which was otherwise carried out as was Test XXIX above.

TABLE XL

| Compound of Example No. | Rate | A | B | C |
|---|---|---|---|---|
| 1 | 10 ppm | 1 | 1 | 1 |
|  | 100 | 7.5 | 9 | 5 |
| 2 | 10 | 1 | 1.5 | 1 |
|  | 100 | 8 | 9 | 2 |
| 10 | 10 | 1 | 1 | 1 |
|  | 100 | 2 | 8 | 2 |

Test XLI

In this test, the compound of Example 1 was used, formulated substantially as in Test I, and some plants were sprayed in a band on an upper leaf surface, and others in a band on a lower leaf surface. The following results were obtained by reading the side of the leaf opposite the spray.

TABLE XLI

| Rate | Upper A | Upper B | Upper C | Lower A | Lower B | Lower C |
|---|---|---|---|---|---|---|
| 200 ppm | 8 | 8 | 1 | 9 | 9 | 3 |
| 400 | 8 | 8 | 1 | 9 | 9 | 5 |
| 600 | 8 | 8 | 2 | 8 | 8 | 7 |
| 800 | 8 | 8 | 2 | 9 | 8 | 7 |
| 1000 | 8 | 8 | 3 | 9 | 9 | 9 |

Test XLII

Compounds of the invention were formulated substantially as described in Test I at 1000 ppm. concentration, and were applied to squash leaves in the systemic test described above. The compound of Example 1 was tested multiple times at this concentration.

TABLE XLII

| Compound of Example No. | A | B | C |
|---|---|---|---|
| 1 | 9 | 9 | 8 |
| 1 | 9 | 9 | 6 |
| 2 | 9 | 9 | 8 |
| 3 | 9 | 9 | 1 |

Field Tests

Test XLIII

Bush summer squash was planted on coarse sandy loam on August 8, in the southeastern U.S.A. The plants were planted in rows, six feet apart, and each test plot was made up of a fifteen foot section of one row. The compound of Example 1, formulated as emulsifiable concentrate M containing 1 pound of compound per gallon, was diluted to the concentrations shown in the table below, and the emulsions were applied to the plants at the volume rate of 50 gallons per acre on September 25, October 3, October 11, October 19 and October 25. No crop injury to the plants was present. The untreated plants were infected with downy mildew to the extent of about 75% of the foliage. The compound's control of downy mildew was observed with the following results.

TABLE XLIII

| Rate | Disease Control | |
|---|---|---|
| | Oct. 1 | Nov. 1 |
| 150 ppm. | 95% | 70% |
| 250 | 83 | 52 |
| 500 | 87 | 57 |
| 1000 | 99 | 45 |

Test XLIV

Tobacco plants were transplanted into a field in the southeastern U.S.A. on May 1, and the plants were treated with the compound of Example 1 on July 6. The compound was supplied in the form of a 1 lb./gal. emulsifiable concentrate, which was diluted with water for application. Some plants were treated by spraying their foliage with 200 ml. per plant of an emulsion containing the compound at the concentrations shown in the table below. Other plants were treated by injecting 75 ml. of emulsion per plant into the soil about 6 inches from the base of the plant and 4-6 inches deep; the emulsion was divided into three portions which were injected at three evenly placed sites about the plant. The concentration of the sub-soil treatments was adjusted to provide the amount of compound per plant indicated in the table below. The compounds were observed on July 13, and on July 25. No injury caused by the compound was seen on either observation date. The disease control achieved by the compound is reported in the table below.

TABLE XLIV

| Rate | Disease Control | |
|---|---|---|
| | July 13 | July 25 |
| 150 ppm. foliar | 88% | 82% |
| 250 | 95 | 94 |
| 500 | 100 | 100 |
| 1000 | 100 | 98 |
| 10 mg./plant sub-soil | 63 | 77 |
| 20 | 38 | 55 |
| 40 | 27 | 27 |

Test XLV

Tobacco was transplanted into the field in the southeastern U.S.A. on March 28, and on the same day the plants were treated with the compounds of Examples 1 and 2. The compounds were supplied as 1 lb./gal. emulsifiable concentrates, which were diluted and the resulting emulsions were applied to the soil around each plant. The formulations were formulae K and G below. The concentration of the emulsions was adjusted to provide the amount of compound shown in the table below in 200 ml. of emulsion per plant, which was poured slowly and evenly over a 6 inch diameter area around the base of each plant. Injury caused by the compounds was measured by counting the mortality in the plants on April 8, compared to the untreated controls. The following results were seen.

TABLE XLV

| Compound of Example No. | Rate | Mortality |
|---|---|---|
| Control | | 16% |
| 1 | 25 mg./plant | 16 |
| 1 | 50 | 32 |
| 1 | 100 | 28 |
| 1 | 150 | 28 |
| 1 | 200 | 36 |
| 1 | 400 | 64 |
| 2 | 25 | 32 |
| 2 | 50 | 12 |
| 2 | 100 | 32 |
| 2 | 150 | 40 |
| 2 | 200 | 48 |
| 2 | 400 | 56 |

Test XLVI

Tobacco plants were transplanted into field plots in the southeastern U.S.A. on May 1, and were treated on July 6 with the compound of Example 1. The compound was supplied as a 1 lb./gal. emulsifiable concentrate, which was diluted with water, and the emulsions were applied to the soil in a 12-inch-diameter area around the base of each plant. The concentration and amount of emulsion were adjusted to provide the amount of compound per plant shown below; the amount of emulsion ranged from 250 to 475 ml./plant. The plants were observed on July 13 and July 25. No injury to any of the plants was evident on either date. The untreated control plants were heavily infected with black shank, to the extent of from 60% to 95% involvement. Disease control achieved by the compounds was as follows on the two observation dates.

TABLE XLVI

| Rate | July 13 | July 25 |
|---|---|---|
| 112 mg./plant | 100% | 100% |
| 225 | 95 | 95 |

TABLE XLVI-continued

| Rate | July 13 | July 25 |
|------|---------|---------|
| 474  | 95      | 95      |

Test XLVII

Field plots on coarse sandy loam in the southeastern U.S.A. were prepared by applying the compounds of Examples 1 and 2, supplied as 1 lb./gal. emulsifiable concentrates K and G, at the rates shown in the table below. The formulations were diluted so that all applications were made at the volume rate of 50 gallons per acre. As soon as the compounds were applied, they were incorporated into the soil with a tiller. Tobacco seedlings were transplanted into the plots on March 28 in rows six feet apart. Each test plot constituted 50 feed of one row. On April 8, the number of live plants in each plot was counted, and expressed as a percentage, based on the number of plants in the control plots as 100%.

TABLE XLVII

| Compound of Example No. | Rate | Result |
|---|---|---|
| 1 | 0.5 lb./A. | 96% |
| 1 | 1 | 100 |
| 1 | 1.5 | 110 |
| 1 | 2 | 105 |
| 2 | 0.5 | 94 |
| 2 | 1 | 116 |
| 2 | 1.5 | 113 |
| 2 | 2 | 116 |

Test XLVIII

Niagara grape plants were transplanted into medium sandy clay on May 5 in the midwestern U.S.A. The plants' foliage was treated with spray applications of the compound of Example 1 on June 13, June 20, June 26, July 3 and July 10. The compound was supplied as 1 lb./gal. emulsifiable concentrate M and was diluted to the concentrations shown in the table below. Each test plot was made up of three plants and 1 liter of emulsion was applied to the three plants. The plants were observed on June 21, July 9, July 17, and August 2. No injury was observed, except for a minor amount of injury on June 21 in the 250 ppm. plot only.

The control plants were infected with downy mildew, to a degree ranging from about 35% at the first observation to about 60% at the last observation. Disease control was as follows.

TABLE XLVIII

| | Disease Control | | |
|---|---|---|---|
| Rate | July 9 | July 17 | August 2 |
| 150 ppm. | 60% | 47% | 53% |
| 250 | 75 | 73 | 72 |
| 500 | 94 | 93 | 92 |
| 1000 | 100 | 98 | 96 |

Test XLIX

Bush summer squash were seeded in a 6-foot rows in the southeastern U.S.A., and the compound of Example 1, supplied as 1 lb./gal. emulsifiable concentrate M, was applied in the furrow along with the seeds. The emulsifiable concentrate was diluted so as to supply the amount of compound named in the table below in a volume application of 30 gallons per acre. The seed was planted on September 26, and the crop emergence was observed on October 10. Crop injury was observed on October 18 and on November 1. The results were as follows.

TABLE XLIX

| | | Injury | |
|---|---|---|---|
| Rate | Emergence | October 18 | November 1 |
| 1.2 g./40 ft. | 100% | 57% | 23% |
| 1.75 | 100 | 13 | 0 |
| 3.5 | 10 | 75 | 65 |
| 7.0 | 3 | 92 | 78 |

Test L

Tomato plants were transplanted into field plots in the southeastern U.S.A. on August 16, and the compound of Example 1 was applied on September 25, October 3, October 11, October 19, October 25 and November 6. The compound was supplied as 1 lb./gal. emulsifiable concentrate M, and was diluted to the concentrations shown in the table below and applied to the foliage of the plants at the volume rate of 50 gallons per acre. The field was inoculated with *Phytophthora infestans*, the tomato late blight organism, on October 12. The plants were observed for crop injury on various dates from October 1 to November 5, and no injury was observed. Control of late blight was observed on November 1 and November 5; control of the disease on the foliage and on the fruit was observed separately. The untreated control plants were extensively involved by the disease to the extent of from 45 to 80%. The observed results were as follows.

TABLE L

| | Disease Control | | | |
|---|---|---|---|---|
| | November 1 | | November 5 | |
| Rate | Foliage | Fruit | Foliage | Fruit |
| 150 ppm. | 63% | 48% | 72% | 73% |
| 250 | 72 | 93 | 83 | 95 |
| 500 | 80 | 88 | 87 | 87 |
| 1000 | 82 | 96 | 90 | 95 |

Field Tests

The compounds of Examples 1 and 2 were tested in the midwestern United States against tomato late blight and grape downy mildew. The host plants were grown in several different locations, in a year when the weather was favorable for both diseases and the plants were very intensely infected. Application rates were 125, 250 and 500 ppm. of each compound, and applications were made at both 7- and 14-day intervals.

Good control of the diseases was obtained in some tests, but the results overall were not commercially acceptable. The compounds need to be combined with a long-lasting fungicide to achieve control of intense infections when applied at reasonably long application intervals.

Methods of Use

The compounds of the present invention are particularly valuable when used in the method of this invention, which is a method of reducing the adverse effects of diseases of plants caused by fungi of the Phycomycete group. The Phycomycetes are a well-known class of fungi which cause many disastrous diseases, including late blight of potato. The following typical plant diseases are caused by Phycomycetes and are mentioned, with their causative organisms, to assure that the reader understands the uses of the compounds.

black wart of potato—*Synchtrium endobioticum*
brown spot of maize—*Physoderma zeaemaydis*
crown wart of alfalfa—*Physoderma alfalfae*
root rot of pea—*Aphanomyces euteiches*
Pythium damping-off, root rot, stem rot, soft rot and stalk rot of many crops—*Pythium arnhenomanes, P. aphanidermatum, P. ultimum, P. debaryanum, P. splendens, P. scleroteichum*
milo disease of sorghum—*Periconia circinata*
late blight of potato and tomato—*Phytophthora infestans*
fruit rot of pear and apple—*Phytophthora cactorum*
brown rot of lemon—*Phytophthora citrophthora*
tomato root rot—*Phytophthora cryptogea*
rot of pepper—*Phytophthora capsici*
coconut bud rot—*Phytophthora palmivova*
black shank of tobacco—*Phytophthora parasitica* var. *nicotiniae*
blue mold of tobacco—*Peronospora tabacina*
root rot of cauliflower—*Phytophthora megasperma*
root rot of avocado—*Phytophthora cinnamoni*
white rust—*Albugo candida, A. occidentalis, A. ipomoeaepanduraneae, A. minor, A. tragopogonis*
downy mildew of grass—*Sclerospora graminicola*
downy mildew of grape—*Plasmopara viticola*
downy mildew of onion—*Peronospora destructor*
downy mildew of cucurbits—*Pseudoperonospora cubensis*
downy mildew of lettuce—*Bremia lactucae*

The method of the present invention is carried out by applying a compound of the invention to a plant to be protected from such fungi, or to the soil in which the plant grows. The compounds are effective when applied either before or after infection by such a fungus. The tests reported above show that the interval between treatment and infection can be as much as 7 to 9 days, or even longer, depending on the circumstances.

The method of the invention is effective against Phycomycetes which infect both the foliage and the roots of plants. Accordingly, depending on the disease from which the plants are expected to suffer, the compounds can usefully be applied to the foliage or to the soil in which the plants grow. Further, the compounds can beneficially be applied to seed, in the form of a seed treatment or coating, before the seed is planted. Alternatively, a composition containing a compound of the invention can be applied to the soil in a small area around the seed, by an applicator which is part of the planter, to assure that the compound is in close contact with the soil in which the plant is actually rooted.

Alternatively, when a compound is to be applied to the soil, it may be advantageous to carry the compound, or the composition containing the compound, into the soil with a large amount of water to assure contact with the roots and the soil immediately around the roots.

When a plant protectant is applied to foliage, it is customary to measure the dosage of the compound by its concentration in the dispersion which is actually applied. The reason is that the amount of the dispersion retained on the leaves is essentially constant, and depends primarily on the area of the foliage. Thus, the amount of compound applied can be varied only by varying the concentration of it in the dispersion. In general, the concentration of compounds of the present invention in spray dispersions is in the range of from about 1 part per million (ppm.) to about 1,000 ppm., depending on the identity of the compound, the severity of the infection which is present or is expected, the organism of primary concern, the weather and other factors known to plant pathologists. More preferable concentrations are in the range from about 5 ppm. to about 1000 ppm., still more preferably in the range from about 10 ppm. to about 500 ppm.

When a compound is to be applied to the soil, it is often convenient to express the dosage in terms of amount of compound per unit of area. The present compounds are usefully applied to the soil at rates from about 0.1 to about 10 pounds per acre, more preferably at rates from about 0.5 to about 5 pounds per acre. The same factors mentioned above are material to choosing a soil application rate, and in addition the soil type, moisture content and organic content are pertinent to the decision as well.

It will be understood that higher application rates are needed in field-grown crops than are needed in the greenhouse. The compounds are useful in both environments, and the reader who is knowledgeable in plant protection will choose application rates in the higher ranges for field use, and in the lower ranges for greenhouse use. The many tests reported above are helpful in determining application rates.

In earlier days, it was common to apply fungicides and other plant protectants as dusts. Such applications are now seldom used because they are inefficient. However, dusts of the present compounds can be used, and should contain the active ingredient in concentrations in the range of from about 0.5% to about 5%.

It is usual to apply plant protectants to a crop several times in the course of a season. The same practice should be followed in using the present compounds. The interval between applications depends on the weather, the severity of infection and the rate at which the crop is growing. In general, intervals of from several days to a few weeks are appropriate. Preferably, the interval should be in the range of about 5-15 days.

The above preferred concentrations and dosage amounts of the compounds are given for the guidance of the practitioner, but it will be understood by one who has read the tests above that application of a Phycomycete-inhibiting amount of a compound reduces the adverse effects of the disease, even though only a part of the Phycomycete population may be killed by the compound. The term "Phycomycete-inhibiting amount" is used here to describe an amount which is sufficient to reduce the adverse effects of a Phycomycetous fungus. The term "reducing the adverse effects" refers to weakening the pathogen sufficiently that its reproduction rate and its vigor are decreased, with the result that the express signs of the disease, and the resulting injury to the host plant, are decreased.

Agricultural chemists and farmers know of a great many adjuvants used to improve the spreading and sticking of agricultural compounds on foliage. Such additives are customarily sold under trade-names, such as "AGRIMUL 26B", "AGRIWET FR", "CODICIDE OIL", "JONCRYL 77", "ENHANCE" "NU-FILM 17", "TACK SYSTEM 5", "HERB-AD", "AD-WET", "PEN-A-TRATE", "BIVERT" and many others. Such conventional adjuvants, which are commercially available to farmers, may be used in conjunction with foliar applications of the present compounds and will improve their activity and extend the period between applications of the compound.

It has been discovered, however, that a particular group of adjuvants have a remarkable effect on the activity of the present compounds. These preferred adjuvants are quaternary ammonium salts of trialkoxysilyl alkylamines. The preferred adjuvant is sold by Petrarch Systems, Inc., Bristol, Pa. under the code name "C-09745". It is octadecyldimethyl-[3-(trimethoxysilyl)propyl]ammonium chloride.

Use of an adjuvant such as C-09745 both reduces the necessary application rate of a compound of this invention and extends its residual life, so that the interval between applications may be extended. It is advisable to add from about 0.01% to about 0.1% of an adjuvant such as "C-09745" to the complete spray mixture. The higher part of the range of rates is preferred, such as from about 0.05% to about 0.1%.

It will be seen that considerably more adjuvant than compound is usually used. Thus, it is not preferred to include the adjuvant in a composition according to the invention, but, rather, simply to add the adjuvant to the spray tank immediately before application. Adjuvants such as "C-09745" are not particularly stable in water, so it is not advisable to prepare a spray mixture containing such an adjuvant in advance of its use.

A few tests in which C-09745 was used as an adjuvant will be reported to illustrate the value of application with such an adjuvant.

Test A

Compounds of the invention were tested against downy mildew of grapes in greenhouse tests carried out substantially as were the greenhouse tests described above. Various formulations of the compounds of Examples 1 and 2 were used, and Petrarch "C-09745" adjuvant was added to the spray mixtures in the concentrations shown below. In some tests, the plants were inoculated with the disease organisms about 4 hours after the treatments were applied, and in other tests the inoculations were delayed for 72 or 168 hours. The results were as follows.

TABLE A

| Compound of Ex. No. | Formulation | Rate ppm. | Adjuvant | 4 Hr. | 72 Hr. | 168 Hr. |
|---|---|---|---|---|---|---|
| 1 | K | 6.25 | 0 | 1 | 1 | |
|  |  | 12.5 |  | 5 | 1 | |
|  |  | 25 |  | 5 | 1 | |
|  |  | 6.25 | 0.1% | 9 | 7 | |
|  |  | 12.5 |  | 9 | 7 | |
|  |  | 25 |  | 9 | 8 | |
|  |  | 3.12 | 0 | 1 | 1 | |
|  |  | 6.25 |  | 1 | 1 | |
|  |  | 12.5 |  | 5 | 1 | |
|  |  | 3.12 | 0.1% | 7 | 8 | |
|  |  | 6.25 |  | 9 | 8 | |
|  |  | 12.5 |  | 9 | 9 | |
| 2 | G | 3.12 | 0 | 1 | 1 | |
|  |  | 6.25 |  | 1 | 1 | |
|  |  | 12.5 |  | 8 | 1 | |
|  |  | 3.12 | 0.1% | 8.5 | 8.5 | |
|  |  | 6.25 |  | 8 | 9 | |
|  |  | 12.5 |  | 9 | 9 | |
|  |  | 0 |  | 9 | 7 | |
| 1 | K | 3.12 | 0 | 1 | 1 | |
|  |  | 6.25 |  | 4 | 1 | |
|  |  | 3.12 | 0.1% | 9 | 4 | |
| 2 | G | 3.12 | 0 | 1 | 1 | |
|  |  | 6.25 |  | 8 | 1 | |
|  |  | 3.12 | 0.1% | 8.5 | 8.5 | |
| 1 | K | 3.12 | 0 | 1 | 1 | |
|  |  | 6.25 |  | 1 | 1 | |
|  |  | 3.12 | 0.1% | 7 | 4 | |
|  | P | 3.12 | 0 | 1 | 1 | |
|  |  | 6.25 |  | 1 | 1 | |
|  |  | 3.12 | 0.1% | 8 | 8.9 | |
| 2 | G | 3.12 | 0 | 1 | 1 | |
|  |  | 6.25 |  | 5 | 1 | |
|  |  | 3.12 | 0.1% | 6 | 8 | |
|  | A | 3.12 | 0 | 1 | 1 | |
|  |  | 6.25 |  | 1 | 1 | |
|  |  | 3.12 | 0.1% | 8 | 5 | |
| 1 | K | 50 | 0 |  | 4 | 4 |
|  |  | 100 |  |  | 4 | 4 |
|  |  | 50 | 0.05% |  | 9 | 4 |
|  |  | 100 |  |  | 4 | 4 |
| 2 | G | 50 | 0 |  | 4 | 4 |
|  |  | 100 |  |  | 4 | 4 |
|  |  | 50 | 0.05% |  | 4 | 4 |
|  |  | 100 |  |  | 4 | 4 |
|  |  | 0 | 0.05% |  | 8 | 7 |

Test B

The compounds of Examples 1 and 2 were tested against downy mildew of cucumbers in tests carried out substantially as were the above tests against the same organism. The preferred adjuvant was added to the spray mixtures at the indicated concentrations below, and the treated plants were inoculated with the disease organism either 2-4 hours or 48 hours after treatment. In several tests, some of the plants were exposed to artificial rain to determine if the compound was washed off the foliage. The results were as follows.

TABLE B

| Compound of Ex. No. | Formulation | Rate ppm. | Adjuvant | 2-4 Hours Rain | 2-4 Hours No Rain | 48 Hours Rain | 48 Hours No Rain |
|---|---|---|---|---|---|---|---|
| 1 | K | 1 | 0 | 1 | 1 | | |
|  |  | 3 |  | 8 | 8 | | |
|  |  | 1 | 0.05% | 8 | 9 | | |
|  |  | 3 |  | 9 | 9 | | |
|  |  | 0 |  | 4 | 6 | | |
|  |  | 0.5 | 0 | 1 | 4 | | |
|  |  | 1 |  | 4 | 6 | | |
|  |  | 3 |  | 8 | 9 | | |
|  |  | 0.5 | 0.025% | 9 | 9 | | |
|  |  | 1 |  | 9 | 9 | | |
|  |  | 3 |  | 9 | 9 | | |
|  | P | 0.5 | 0 | 1 | 1 | | |
|  |  | 1 |  | 1 | 1 | | |
|  |  | 3 |  | 1 | 4 | | |

TABLE B-continued

| Compound of Ex. No. | Formu-lation | Rate ppm. | Adjuvant | 2-4 Hours | | 48 Hours | |
|---|---|---|---|---|---|---|---|
| | | | | Rain | No Rain | Rain | No Rain |
| | | 0.5 | 0.025% | 6 | 9 | | |
| | | 1 | | 6 | 9 | | |
| | | 3 | | 9 | 9 | | |
| | | 0 | | 3 | 8 | | |
| | K | 0.5 | 0 | 1 | 1 | 1 | 1 |
| | | 1 | | 4 | 1 | 1 | 1 |
| | | 0.5 | 0.012% | 4 | 4 | 1 | 4 |
| | | 1 | | 8 | 6 | 1 | 4 |
| | P | 0.5 | 0 | 1 | 1 | 1 | 1 |
| | | 1 | | 1 | 1 | 1 | 1 |
| | | 0.5 | 0.012% | 4 | 1 | 1 | 4 |
| | | 1 | | 7 | 1 | 1 | 4 |
| | K | 0.5 | 0.025% | 8 | 6 | 1 | 7 |
| | | 1 | | 7 | 7 | 1 | 4 |
| | P | 0.5 | | 7 | 6 | 1 | 4 |
| | | 1 | | 7 | 4 | 1 | 5 |
| | | 0 | 0.012% | 1 | 4 | 1 | 4 |
| | | | 0.025% | 1 | 1 | 1 | 1 |
| 2 | G | 1 | 0 | 4 | | | |
| | | 1 | 0.1% | 9 | | | |

The Combinations

An important embodiment of the present invention is a group of fungicidal combination compositions and fungicidal methods which comprise a compound of the invention in combination with a dithiocarbamate fungicide. The general formula of the dithiocarbamates was described above in the Summary of the Invention.

Certain classes of the dithiocarbamates are particularly preferred for use in the present combinations. It will be understood that the following preferred classes of dithiocarbamates may be combined with any of the preferred classes of compounds of the invention to obtain preferred classes of combinations.

A preferred group of dithiocarbamates is that wherein M is a zinc ion, a manganese ion or a coordination complex of both. Another preferred class is that wherein $M^1$ is a sodium or a ferric ion. Further preferred classes of dithiocarbamates are those wherein $R^8$ is ethylene; wherein $R^9$ is hydrogen or methyl; and that wherein $R^{10}$ is methyl.

Particular dithiocarbamate fungicides which are preferred are ferbam, nabam, maneb, mancozeb, zineb, and ziram. Maneb and mancozeb are particularly preferred.

The combinations are used on the same plants, and for the control of the same diseases, as are the compounds of the invention. Use of the combinations, particularly combinations including the preferred dithiocarbamates with the preferred compounds of the invention, extends the interval between applications of fungicide, and allows the use of lower application rates. Thus, use of a compound of the invention in combination with a dithiocarbamate allows acceptable Phycomycete control for a period of about 7-14 days, depending on the weather and the severity of the infection which is encountered.

When a combination is used in the field, the preferred foliar application rate is in the range of from about 50 to about 250 g./ha. of the compound of the invention, plus from about 1,200 to about 1,500 ppm. of the dithiocarbamate. If the application is measured by concentration in the spray mixture, rather than in weight per land area, the absolute numbers are the same—about 50-250 ppm. of compound of this invention plus about 1,200-1,500 ppm. of dithiocarbamate. Higher rates can, of course, be used, such as from about 250 to about 1,000 g./ha. or ppm. of compound of the invention, and about 1,500-2,500 g./ha. or ppm. of dithiocarbamate. In general, however, it will be found that application rates in the preferred range of rates are effective, and are, of course, more economical and free of side effects than are higher application rates. It has already been shown that the use of adjuvants, particularly the quaternary ammonium silyl adjuvants, increase the activity of the compounds of the invention and extend the period between spray appications. The same fact is true of the combinations with dithiocarbamates, and the use of such adjuvants with the combinations is a particularly preferred embodiment of the invention.

The dithiocarbamate fungicides are very well known in agricultural chemistry, and formulations of them are available as articles of commerce. Such formulations may be used in preparing the present combinations, as by simply adding formulations of the dithiocarbamate and the compound of the invention to a conventional spray tank. Equally, combination formulations may be prepared, in which both compounds are present at a convenient ratio, such as, for example, 10 parts of dithiocarbamate and 1 part of compound of the invention. Such combination formulations offer no particular difficulties to an agricultural chemist and are prepared on the same principles as are formulations of compounds of the invention, which are extensively discussed above.

Combination Tests

The following greenhouse tests were carried out to ascertain the efficacy of representative combinations of dithiocarbamates and compounds of the invention, against representative phycomycete diseases.

Test 1

Combinations of the compound of Example 2 with maneb were evaluated against downy mildew of squash. The combinations were supplied as formulation Y, and the compound alone was supplied as formulation 02. The test method was the same as that of previously reported greenhouse tests against the same disease. Plants were inoculated 4 hours or 48 hours after they were sprayed with dispersions of the compound or the combination. Some of the plants were exposed to ½ inch of artificial rain before inoculation with the disease.

TABLE 1

| Rate, ppm. | | 4 Hrs. | | |
|---|---|---|---|---|
| Compound | Maneb | Rain | No Rain | 48 Hrs. |
| 10 | 0 | 9 | 9 | 9 |
| 5 | | 9 | 9 | 8 |
| 1 | | 1 | 9 | 4 |
| 10 | 60 | 8 | 9 | 9 |
| 5 | 30 | 1 | 9 | 9 |
| 1 | 6 | 1 | 1 | 7 |

Test 2

The compound of Formula 1, supplied as formulation M, was tested in combination with maneb against downy mildew of squash. The tests were carried out as described in Test 1 above. However, the maneb was supplied as technical compound which was formulated in the manner of Test I of the present specification.

TABLE 2

| Rate, ppm. | | 4 Hrs. | | |
|---|---|---|---|---|
| Compound | Maneb | Rain | No Rain | 48 Hrs. |
| 1 | 0 | 8 | 8 | 1 |
| 3 | | 9 | 9 | 5 |
| 9 | | 9 | 9 | 5 |
| 1 | 4 | 7 | 9 | 7 |
| 3 | 9 | 9 | 9 | 7 |
| 9 | 27 | 9 | 9 | 9 |

Test 3

The compounds of Examples 1 and 2 were tested in combination with mancozeb against downy mildew of squash. In these tests, the plants were inoculated 4 hours after treatment, and no exposure to rain was used. The compound of Example 1 was supplied as formulation K, and Example 2 was formulation G. The combination of Example 1 and mancozeb was formulation AA, and Example 2 combined with mancozeb was formulation Z.

TABLE 3

| Compound | Rate | | Result |
|---|---|---|---|
| | Compound | Mancozeb | |
| 1 | 1 ppm. | 0 ppm. | 1 |
| | 3 | | 8 |
| | 9 | | 9 |
| | 1 | 6 | 1 |
| | 3 | 18 | 3 |
| | 9 | 54 | 8.3 |
| 2 | 1 | 0 | 1 |
| | 3 | | 8 |
| | 9 | | 8.5 |
| | 1 | 6 | 1 |
| | 3 | 18 | 3 |
| | 9 | 54 | 8 |

Test 4

The compounds of Examples 1 and 2 were tested, in combination with mancozeb, against downy mildew of grapes in greenhouse tests carried out substantially as were the greenhouse grape tests described earlier in the specification. The plants were inoculated 4 and 48 hours after spraying with the treatments. A number of different formulations were used, as indicated in the table below. In some cases, 0.1% of the adjuvant, Petrarch "C-09745", was added to the spray mixtures containing the compound and mancozeb combination; such cases are indicated by "Adj." in the Formulation column.

TABLE 4

| Cpd. of Ex. No. | Rate | | Formulation | 4 Hrs. | 48 Hrs. |
|---|---|---|---|---|---|
| | Compound | Mancozeb | | | |
| 1 | 3.12 ppm. | 0 ppm. | K | 5 | 1 |
| 2 | 3.12 | 0 | G | 5 | 1 |
| 1 | 1.56 | 9.36* | K | 3 | 3 |
| | 3.12 | 18.72* | K | 5 | 6 |
| 1 | 1.56 | 15.6* | K | 8 | 8 |
| | 3.12 | 31.2* | K | 9 | 8 |
| 1 | 1.56 | 9.36 | AA | 7 | 1 |
| | 3.12 | 18.72 | AA | 1 | 1 |
| 1 | 1.56 | 9.36* | K-Adj. | 8 | 6 |
| | 3.12 | 18.72* | K-Adj. | 9 | 9 |
| 1 | 1.56 | 9.36 | AA-Adj. | 7 | 1 |
| | 3.12 | 18.72 | AA-Adj. | 9 | 1 |
| 2 | 1.56 | 9.36* | G | 7 | 3 |
| | 3.12 | 18.72* | G | 9 | 5 |
| 2 | 1.56 | 15.6* | G | 6 | 8 |
| | 3.12 | 31.2* | G | 9 | 9 |
| 2 | 1.56 | 9.36 | Z | 1 | 1 |
| | 3.12 | 18.72 | Z | 4 | 1 |
| 2 | 1.56 | 9.36* | G-Adj. | 9 | 9 |
| | 3.12 | 18.72* | G-Adj. | 9 | 9 |
| 2 | 1.56 | 9.36 | Z-Adj. | 5 | 3 |
| | 3.12 | 18.72 | Z-Adj. | 9 | 6 |

*Mancozeb was supplied as commercial 37% suspension.

Test 5

The compound of Example 2, supplied in the form of formulation 02, was tested against downy mildew of grapes along with the combination of the compound of Example 2 and maneb, in the form of formulation Y. Inoculations with the disease were made 4 hours after treatment, with and without exposure to artificial rain, and also 168 hours after treatment.

TABLE 5

| Rate, ppm. | | 4 Hrs. | | |
|---|---|---|---|---|
| Compound | Maneb | Rain | No Rain | 168 Hrs. |
| 50 | 0 | 9 | 9 | 6 |
| 100 | 0 | 9 | 9 | 7 |
| 50 | 300 | 6 | 9 | 7 |
| 100 | 600 | 9 | 7 | 8 |

Test 6

The compound of Example 1 was tested against downy mildew of grapes in combination with mancozeb. Two formulations of Example 1 were used in the tests, and mancozeb was supplied as commercial 37% suspension. In one instance, Petrarch "C-90745" adjuvant was added to the spray mixture; this instance is indicated by "Adj." in the formulation column. No artificial rain was used on the treated plants, and plants were inoculated on the same day as the treatment and on the third, fifth and sixth days thereafter.

TABLE 6

| Rate, ppm. | | Formulation | 0 Day | 3 Days | 5 Days | 6 Days |
|---|---|---|---|---|---|---|
| Compound | Mancozeb | | | | | |
| 12.5 | 0 | M | 5 | | 1 | |
| 25 | | | 9 | | 1 | |
| 50 | | | 9 | | 1 | |
| 100 | | | 9 | | 1 | |
| 6.25 | 25 | | 9 | | 1 | |
| 12.5 | 50 | | 9 | | 5 | |
| 25 | 100 | | 9 | | 5 | |
| 50 | 200 | | 9 | | 7 | |
| 100 | 400 | | 9 | | 8 | |
| 100 | 0 | K | 4 | | 5 | |

TABLE 6-continued

| Rate, ppm. | | | | | | |
|---|---|---|---|---|---|---|
| Compound | Mancozeb | Formulation | 0 Day | 3 Days | 5 Days | 6 Days |
| 10 | 100 | K | | 8.5 | | 9 |
| 10 | 100 | K-Adj. | | 9 | | 9 |

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form wettable granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 10% to about 50% by weight of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to about 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

The following typical formulations of compounds of the invention have been prepared, and are typical of compositions useful in the practice of the present invention.

A. 50% Wettable Powder

| | |
|---|---|
| Compound of Example 2 | 52.08% |
| Sodium Lauryl Sulfate | 5.00 |
| Purified Silica | 5.00 |
| Lignin Sulfonate | 5.00 |
| Kaolin | 32.92 |

The ingredients were mixed and ground through an air-impact mill.

B. 1 lb./gal. Suspension

| | |
|---|---|
| Compound of Example 1 | 12.5% |
| Precipitated Silica | 1.0 |
| 2% Xanthan Solution | 10.0 |
| Antifoam | 0.2 |
| Lignin Sulfonate | 0.5 |
| "POLYFON MT-603" (hydrophobic rosin) | 4.5 |
| Ethylene glycol | 4.5 |
| "TERGITOL TMN-6" (nonionic surfactant) | 1.0 |
| Water | 65.8 |

The product was ground in an attrition mill.

C. 1 lb./gal. Suspension

| | |
|---|---|
| Compound of Example 1 | 12.5% |
| Precipitated Silica | 1.0 |
| Antifoam | 0.2 |
| 2% Xanthan Solution | 10.0 |
| "MAKON 10" (nonionic surfactant) | 3.0 |
| Diamond Shamrock "2314-VI-26" (polymeric emulsion) | 1.0 |
| Water | 72.3 |

The product was ground in an attrition mill until 50% of the particles were smaller than 1.5 microns.

D. 1 lb./gal. Suspension

| | |
|---|---|
| Compound of Example 1 | 12.5% |
| Precipitated Silica | 1.0 |
| Antifoam | 0.2 |
| 2% Xanthan Solution | 10.0 |
| "MAKON 10" (nonionic surfactant) | 4.0 |
| Water | 72.3 |

The product was ground in an attrition mill until 50% of the particles were smaller than 1.5 microns.

E. 1 lb./gal. Suspension

| | |
|---|---|
| Compound of Example 1 | 12.5% |
| Precipitated Silica | 1.0 |
| Antifoam | 0.2 |
| "MAKON 10" (nonionic surfactant) | 3.0 |
| 2% Xanthan Solution | 10.0 |
| "POLYFON MT-803" (hydrophobic rosin) | 1.0 |
| Water | 72.3 |

The product was ground in an attrition mill until 50% of the particles were smaller than 1.5 microns.

F. 1 lb./gal. Suspension

| | |
|---|---|
| Compound of Example 2 | 12.5% |
| Precipitated Silica | 1.0 |
| Antifoam | 0.2 |
| 2% Xanthan Solution | 10.0 |
| "MAKON 10" (nonionic surfactant) | 3.0 |
| Hydrophobic Rosin | 1.0 |
| Water | 72.3 |

The hydrophobic rosin was Polyfon "MT-603" in batch F1 and was Polyfon "MT-803" in batch F2. The product was ground in an attrition mill until 50% of the particles were smaller than 1.5 microns.

G. 1 lb./gal. Emulsifiable Concentrate

| | |
|---|---|
| Compound of Example 2 | 11.6% |
| Aromatic Naphtha | 84.4 |
| "TOXIMUL D" (surfactant blend) | 2.0 |
| "SPONTO AD6-29" (nonionic surfactant) | 2.0 |

H. 1 lb./gal. Emulsifiable Concentrate

| | |
|---|---|
| Compound of Example 2 | 12.4% |
| Propylene Glycol, Methyl Ether | 12.2 |
| Aromatic Naphtha | 65.4 |
| "TOXIMUL H" (nonionic surfactant) | 9.5 |
| "TOXIMUL D" (surfactant blend) | 0.5 |

I. 3 lb./gal. Emulsifiable Concentrate

| | |
|---|---|
| Compound of Example 1 | 37.5% |
| Acetophenone | 57.5 |
| "SPONTO AD6-29" (nonionic surfactant) | 5.0 |

J. 2 lb./gal. Emulsifiable Concentrate

| | |
|---|---|
| Compound of Example 1 | 25.0% |
| Acetophenone | 69.5 |
| "SPONTO AD6-29" (nonionic surfactant) | 5.0 |
| "MAKON 10" (nonionic surfactant) | 0.5 |

K. 2 lb./gal. Emulsifiable Concentrate

| | |
|---|---|
| Compound of Example 1 | 25.0% |
| Aromatic Naphtha | 70.0 |
| "TOXIMUL D" (surfactant blend) | 2.5 |
| SPONTO AD6-29" (nonionic surfactant) | 2.5 |

L. 1.5 lb./gal. Emulsifiable Concentrate

| | |
|---|---|
| Compound of Example 2 | 18.75% |
| Aromatic Naphtha | 75.25 |
| "TOXIMUL D" (surfactant blend) | 3.0 |
| SPONTO AD6-29" (nonionic surfactant) | 3.0 |

M. 1 lb./gal. Emulsifiable Concentrate

| | |
|---|---|
| Compound of Example 1 | 12.2% |
| Propylene Glycol, Methyl Ether | 12.2 |
| Aromatic Naphtha | 65.6 |
| "TOXIMUL H" (nonionic surfactant) | 10.0 |

N. 1 lb./gal. Emulsifiable Concentrate

| | |
|---|---|
| Compound of Example 2 | 11.6% |
| Aromatic Naphtha | 85.4 |
| "TOXIMUL D" (surfactant blend) | 1.5 |
| "SPONTO AD6-29" (nonionic surfactant) | 1.5 |

O. 1 lb./gal. Suspension

| | |
|---|---|
| Compound of Example 2 | 12.5% |
| Precipitated Silica | 1.0 |
| Antifoam | 0.2 |
| 2% Xanthan Solution | 10.0 |
| "MAKON 10" (nonionic surfactant) | 3.0 |
| Water | 72.3 |

Batch 01 contained 1% of additional "MAKON 10", and batch 02 contained 1% of Diamond Shamrock "2314-IV-26" (polymeric emulsion). The products were ground in an attrition mill until a stable suspension was achieved.

P. 50% Wettable Powder

| | |
|---|---|
| Compound of Example 1 | 52.1% |
| Sodium Lauryl Sulfate | 5.0 |
| Precipitated Silica | 5.0 |
| Lignin Sulfonate | 5.0 |
| Kaolin | 32.9 |

Q. 2 lb./gal. Emulsifiable Concentrate

| | |
|---|---|
| Compound of Example 1 | 24.8% |
| Aromatic Naphtha | 70.2 |
| "TOXIMUL H" (nonionic surfactant) | 2.5 |
| "TOXIMUL D" (surfactant blend) | 2.5 |

R. 1 lb./gal. Emulsifiable Concentrate

| | |
|---|---|
| Compound of Example 2 | 12.5% |
| Aromatic Naphtha | 83.5 |
| "TOXIMUL H" (nonionic surfactant) | 2.0 |
| "TOXIMUL D" (surfactant blend) | 2.0 |

S. 1 lb./gal. Suspension

| | |
|---|---|
| Compound of Example 1 | 12.5% |
| Precipitated Silica | 1.0 |
| 2% Xanthan Solution | 10.0 |
| Antifoam | 0.2 |
| "MAKON 10" (nonionic surfactant) | 3.0 |
| "POLYFAC MT803" (hydrophobic rosin) | 1.0 |
| Water | 72.3 |

The product was ground in an attrition mill.

T. 2 lb./gal. Emulsifiable Concentrate

| | |
|---|---|
| Compound of Example 1 | 22.75% |
| Aromatic Naphtha | 71.25 |
| "SPONTO AD6-29" (nonionic surfactant) | 2.50 |
| "TOXIMUL D" (surfactant blend) | 2.50 |
| Petrarch "C-09745" (silane surfactant) | 1.00 |

U. 1 lb./gal. Emulsifiable Concentrate

| | |
|---|---|
| Compound of Example 2 | 11.6% |
| Aromatic Naphtha | 83.4 |
| "SPONTO AD6-29" (nonionic surfactant) | 2.0 |
| "TOXIMUL D" (surfactant blend) | 2.0 |
| Petrarch "C-09745" (silane surfactant) | 1.0 |

V. 3 lb./gal. Suspension

| | |
|---|---|
| Compound of Example 1 | 33.33% |
| Antifoam | 0.15 |
| "MAKON 10" (nonionic surfactant) | 1.50 |
| 2% Xanthan Solution | 8.00 |
| Preservative | 0.20 |
| Lignin Sulfonate | 0.20 |
| Precipitated Silica | 1.00 |
| Propylene Glycol | 3.50 |
| Water | 52.12 |

The product was ground in an attrition mill.

W. 2 lb./gal. Suspension

| | |
|---|---|
| Compound of Example 2 | 22.00% |
| Antifoam | 0.15 |
| "TERGITOL 25-L-9" (nonionic surfactant) | 1.50 |
| Propylene Glycol | 3.75 |
| Preservative | 0.20 |
| Veegum (calcium magnesium silicate) | 1.00 |
| Xanthan | 0.20 |
| Diamond Shamrock "2314-VI-26" (polymeric emulsion) | 1.50 |
| Water | 69.70 |

X. Combination Suspension

| | |
|---|---|
| Compound of Example 1 | 1.88% |
| Maneb | 7.50 |
| Precipitated Silica | 0.75 |
| Antifoam | 0.15 |
| 2% Xanthan Gum | 7.50 |
| "MAKON 10" (nonionic surfactant) | 2.25 |
| "POLYFON MT-803" (hydrophobic rosin) | 0.75 |
| Water | 79.22 |

The product was ground in an attrition mill until 50% of the particles were smaller than 2 microns by Coulter Counter.

Y. Combination Suspension

| | |
|---|---|
| Compound of Example 2 | 1.88% |

The rest of the formula was indentical to Composition X.

Z. Combination Suspension

| | |
|---|---|
| Compound of Example 2 | 5.4% |
| "MAKON 10" (nonionic surfactant) | 1.0 |
| Water | 5.6 |
| "DITHANE FZ" (mancozeb 37% suspension) | 88.0 |

The compound, water and Makon were combined and ground in attrition mill, and the ground suspension was mixed with Dithane.

AA. Combination Suspension

| Compound of Example 1 | 5.4% |

The rest of the formula was identical to that of Composition Z.

We claim:

1. A compound of the formula

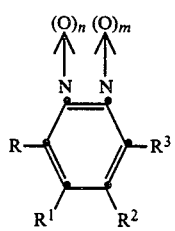

wherein
R³ is chloro, bromo, methyl, cyano or iodo;
R is chloro, bromo, iodo, methyl, cyano or furan-2-ylmethoxy;
R¹ is hydrogen, methyl, ethyl or n-propyl;
R² is

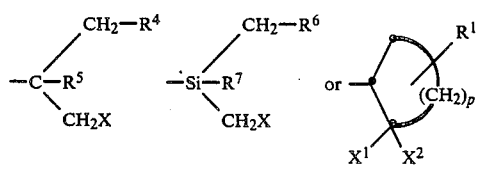

X is fluoro, chloro, bromo or iodo;
X¹ and X² independently represent X or hydrogen, provided that no more than one of X¹ and X² is hydrogen;
R⁴ is hydrogen, chloro, bromo, methyl or ethyl;
R⁵ is hydrogen, chloro, methyl, ethyl, chloromethyl or dichloromethyl;
or R⁴ and R⁵ combine with the group to which they are attached to form a $C_3$-$C_7$ cycloalkyl group substituted with a R¹ group;
R⁶ is hydrogen, chloro, bromo, methyl or ethyl;
R⁷ is hydrogen, methyl, ethyl, chloromethyl or dichloromethyl;
one of m and n is 0 or 1, and the other is 0;
p is 0-4.

2. A compound of claim 1 wherein R¹ is hydrogen.

3. A compound of claim 1 wherein R is chloro, bromo or methyl.

4. A compound of claim 1 wherein R³ is chloro, bromo or methyl.

5. A compound of claim 1 wherein m and n are 0.

6. A compound of claim 1 wherein R² is

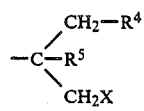

7. A compound of claim 6 wherein X is chloro or bromo.

8. A compound of claim 7 wherein R¹ is hydrogen, and m and n are 0.

9. A compound of claim 8 wherein R and R³ are independently chloro, bromo or methyl.

10. The compound of claim 1 which is 3,6-dichloro-4-(1-chloromethyl-1-methylethyl)pyridazine.

11. The compound of claim 1 which is 3,6-dichloro-4-(1-bromomethyl-1-methylethyl)pyridazine.

12. The compound of claim 1 which is 3,6-dibromo-4-(1-bromomethyl)-1-methylethyl)pyridazine.

13. The compound of claim 1 which is 3-bromo-6-chloro-4-(1-chloromethyl-1-methylethyl)pyridazine.

14. The compound of claim 1 which is 3,6-dichloro-4-(1-fluoromethyl-1-methylethyl)pyridazine.

15. A compound of claim 1 of the formula

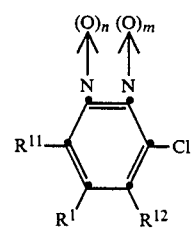

wherein
R¹¹ is chloro or furan-2-ylmethoxy;
R¹² is

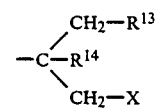

R¹³ is hydrogen, chloro, methyl or ethyl;
R¹⁴ is hydrogen, methyl, ethyl, chloromethyl or dichloromethyl.

16. A fungicidal composition comprising a phytologically-acceptable inert carrier and a compound of claim 1.

17. A fungicidal composition comprising a phytologically-acceptable inert carrier and a compound of claim 7.

18. A fungicidal composition comprising a phytologically-acceptable inert carrier and the compound of claim 10.

19. A fungicidal composition comprising a phytologically-acceptable inert carrier and the compound of claim 11.

20. A fungicidal composition comprising a phytologically-acceptable inert carrier and a compound of claim 15.

21. A method of reducing the adverse effects of Phycomycetous fungi on plants which comprises applying a Phycomycete-inhibiting amount of a compound of claim 1 to the plant or to the soil in which it grows.

22. A method of reducing the adverse effects of Phycomycetous fungi on plants which comprises applying a Phycomycete-inhibiting amount of a compound of claim 7 to the plant or to the soil in which it grows.

23. A method of reducing the adverse effects of Phycomycetous fungi on plants which comprises applying a Phycomycete-inhibiting amount of the compound of claim 10 to the plant or to the soil in which it grows.

24. A method of reducing the adverse effects of Phycomycetous fungi on plants which comprises applying a Phycomycete-inhibiting amount of the compound of claim 11 to the plant or to the soil in which it grows.

25. A method of reducing the adverse effects of Phycomycetous fungi on plants which comprises applying a Phycomycete-inhibiting amount of a compound of claim 15 to the plant or to the soil in which it grows.

26. A fungicidal composition comprising a dithiocarbamate fungicide of the formula

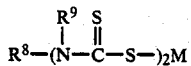

wherein
R$^8$ is C$_1$-C$_4$ alkylene;
R$^9$ is C$_1$-C$_3$ alkyl or hydrogen;
M is a divalent metal ion or two monovalent metal ions;

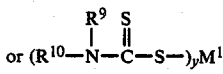

wherein
y is 1-3;
M$^1$ is a metal ion of valence 1-3;
R$^{10}$ is C$_1$-C$_4$ alkyl; and a compound of claim 1.

27. A fungicidal composition comprising a dithiocarbamate fungicide of the formula

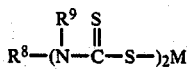

wherein
R$^8$ is C$_1$-C$_4$ alkylene;
R$^9$ is C$_1$-C$_3$ alkyl or hydrogen;
M is a divalent metal ion or two monovalent metal ions;

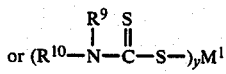

wherein
y is 1-3;
M$^1$ is a metal ion of valence 1-3;
R$^{10}$ is C$_1$-C$_4$ alkyl; and a compound of claim 7.

28. A fungicidal composition comprising a dithiocarbamate fungicide of the formula

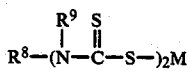

wherein
R$^8$ is C$_1$-C$_4$ alkylene;
R$^9$ is C$_1$-C$_3$ alkyl or hydrogen;
M is a divalent metal ion or two monovalent metal ions;

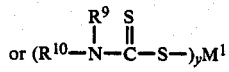

wherein
y is 1-3;
M$^1$ is a metal ion of valence 1-3;
R$^{10}$ is C$_1$-C$_4$ alkyl; and the compound of claim 10.

29. A fungicidal composition comprising a dithiocarbamate fungicide of the formula

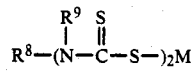

wherein
R$^8$ is C$_1$-C$_4$ alkylene;
R$^9$ is C$_1$-C$_3$ alkyl or hydrogen;
M is a divalent metal ion or two monovalent metal ions;

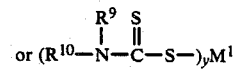

wherein
y is 1-3;
M$^1$ is a metal ion of valence 1-3;
R$^{10}$ is C$_1$-C$_4$ alkyl; and the compound of claim 11.

30. A fungicidal composition comprising a dithiocarbamate fungicide of the formula

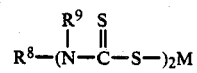

wherein
R$^8$ is C$_1$-C$_4$ alkylene;
R$^9$ is C$_1$-C$_3$ alkyl or hydrogen;
M is a divalent metal ion or two monovalent metal ions;

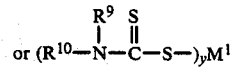

wherein
y is 1-3;
M$^1$ is a metal ion of valence 1-3;
R$^{10}$ is C$_1$-C$_4$ alkyl; and a compound of claim 15.

31. A fungicidal composition comprising ferbam, nabam, maneb, mancozeb, zineb, or ziram and a compound of claim 1.

32. A fungicidal composition comprising ferbam, nabam, maneb, mancozeb, zineb, or ziram and a compound of claim 7.

33. A fungicidal composition comprising ferbam, nabam, maneb, mancozeb, zineb, or ziram and the compound of claim 10.

34. A fungicidal composition comprising ferbam, nabam, maneb, mancozeb, zineb, or ziram and the compound of claim 11.

35. A fungicidal composition comprising ferbam, nabam, maneb, mancozeb, zineb, or ziram and a compound of claim 15.

36. A method of reducing the adverse effects of Phycomycetous fungi on plants which comprises applying to the plant or to the soil in which it grows Phycomycete-inhibiting amounts of a compound of the formula

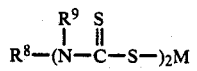

wherein
R$^8$ is C$_1$-C$_4$ alkylene;

$R^9$ is $C_1$-$C_3$ alkyl or hydrogen;

M is a divalent metal ion or two monovalent metal ions;

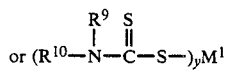

wherein y is 1-3;

$M^1$ is a metal ion of valence 1-3;

$R^{10}$ is $C_1$-$C_4$ alkyl; and of a compound of claim 1.

37. A method of reducing the adverse effects of Phycomycetous fungi on plants which comprises applying to the plant or to the soil in which it grows Phycomycete-inhibiting amounts of a compound of the formula

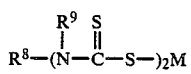

wherein $R^8$ is $C_1$-$C_4$ alkylene;

$R^9$ is $C_1$-$C_3$ alkyl or hydrogen;

M is a divalent metal ion or two monovalent metal ions;

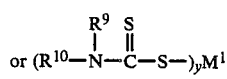

wherein y is 1-3;

$M^1$ is a metal ion of valence 1-3;

$R^{10}$ is $C_1$-$C_4$ alkyl; and of a compound of claim 7.

38. A method of reducing the adverse effects of Phycomycetous fungi on plants which comprises applying to the plant or to the soil in which it grows Phycomycete-inhibiting amounts of a compound of the formula

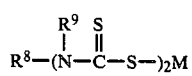

wherein $R^8$ is $C_1$-$C_4$ alkylene;

$R^9$ is $C_1$-$C_3$ alkyl or hydrogen;

M is a divalent metal ion or two monovalent metal ions;

wherein y is 1-3;

$M^1$ is a metal ion of valence 1-3;

$R^{10}$ is $C_1$-$C_4$ alkyl; and of the compound of claim 10.

39. A method of reducing the adverse effects of Phycomycetous fungi on plants which comprises applying to the plant or to the soil in which it grows Phycomycete-inhibiting amounts of a compound of the formula

wherein $R^8$ is $C_1$-$C_4$ alkylene;

$R^9$ is $C_1$-$C_3$ alkyl or hydrogen;

M is a divalent metal ion or two monovalent metal ions;

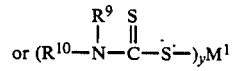

wherein y is 1-3;

$M^1$ is a metal ion of valence 1-3;

$R^{10}$ is $C_1$-$C_4$ alkyl; and of a compound of claim 11.

40. A method of reducing the adverse effects of Phycomycetous fungi on plants which comprises applying to the plant or to the soil in which it grows Phycomycete-inhibiting amounts of a compound of the formula

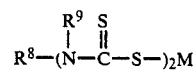

wherein $R^8$ is $C_1$-$C_4$ alkylene;

$R^9$ is $C_1$-$C_3$ alkyl or hydrogen;

M is a divalent metal ion or two monovalent metal ions;

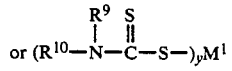

wherein y is 1-3;

$M^1$ is a metal ion of valence 1-3;

$R^{10}$ is $C_1$-$C_4$ alkyl; and of a compound of claim 15.

41. A method of reducing the adverse effects of Phycomycetous fungi on plants which comprises applying to the plant or to the soil in which grows Phycomycete-inhibiting amounts of ferbam, nabam, maneb, mancozeb, zineb or ziram and of a compound of claim 1.

42. A method of reducing the adverse effects of Phycomycetous fungi on plants which comprises applying to the plant or to the soil in which it grows Phycomycete-inhibiting amounts of ferbam, nabam, maneb, mancozeb, zineb or ziram and of a compound of claim 7.

43. A method of reducing the adverse effects of Phycomycetous fungi on plants which comprises applying to the plant or to the soil in which it grows Phycomycete-inhibiting amounts of ferbam, nabam, maneb, mancozeb, zineb or ziram and of the compound of claim 10.

44. A method of reducing the adverse effects of Phycomycetous fungi on plants which comprises applying to the plant or to the soil in which it grows Phycomycete-inhibiting amounts of ferbam, nabam, maneb, mancozeb, zineb or ziram and of the compound of claim 11.

45. A method of reducing the adverse effects of Phycomycetous fungi on plants which comprises applying to the plant or to the soil in which is grows Phycomycete-inhibiting amounts of ferbam, nabam, maneb, mancozeb, zineb or ziram and of a compound of claim 15.

* * * * *